US010647990B2

(12) United States Patent
Lin et al.

(10) Patent No.: US 10,647,990 B2
(45) Date of Patent: May 12, 2020

(54) RICE HIGH TEMPERATURE RESISTANCE GENE AND USE IN CROP BREEDING RESISTANCE TO HIGH TEMPERATURE THEREOF

(71) Applicant: SHANGHAI INSTITUTES FOR BIOLOGICAL SCIENCES, CHINESE ACADEMY OF SCIENCES, Shanghai (CN)

(72) Inventors: Hongxuan Lin, Shanghai (CN); Xinmin Li, Shanghai (CN); Jiping Gao, Shanghai (CN); Junxiang Shan, Shanghai (CN); Min Shi, Shanghai (CN)

(73) Assignee: SHANGHAI INSTITUTES FOR BIOLOGICAL SCIENCES, CHINESE ACADEMY OF SCIENCES, Shanghai (CN)

( * ) Notice: Subject to any disclaimer, the term of this patent is extended or adjusted under 35 U.S.C. 154(b) by 319 days.

(21) Appl. No.: 15/515,630

(22) PCT Filed: May 28, 2015

(86) PCT No.: PCT/CN2015/080119
§ 371 (c)(1),
(2) Date: Sep. 12, 2017

(87) PCT Pub. No.: WO2016/050092
PCT Pub. Date: Apr. 7, 2016

(65) Prior Publication Data
US 2018/0010143 A1    Jan. 11, 2018

(30) Foreign Application Priority Data

Sep. 30, 2014    (CN) .......................... 2014 1 0522280

(51) Int. Cl.
| | |
|---|---|
| *C12N 15/82* | (2006.01) |
| *C07K 14/415* | (2006.01) |
| *A01H 1/04* | (2006.01) |
| *A01H 5/10* | (2018.01) |
| *C12Q 1/6895* | (2018.01) |

(52) U.S. Cl.
CPC ........... *C12N 15/8273* (2013.01); *A01H 1/04* (2013.01); *A01H 5/10* (2013.01); *C07K 14/415* (2013.01); *C12N 15/8205* (2013.01); *C12N 15/8218* (2013.01); *C12N 15/8271* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2013/0167266 A1*   6/2013   He ....................... C07K 14/415
                                                    800/294

FOREIGN PATENT DOCUMENTS

| CN | 101333250 | 6/2012 |
|---|---|---|
| CN | 103421813 | 12/2013 |
| CN | 103288940 | 8/2015 |

OTHER PUBLICATIONS

Hong et al.(Sheng Wu Gong Cheng Xue Bao. Apr. 2010;26(4):509-16) Abstract only.*
Hong et al.(Sheng Wu Gong Cheng Xue Bao. Apr. 2010;26(4):509-16) English translation.*
Smith et al. (Nature Biotechnology, 15:1222-1223, 1997).*
Bork et al. (TIG, 12:425-427, 1996).*
Doerks et al., (TIG, 14:248-250, 1998).*
Sung et al. (Plant Journal, 59:802-812, 2009).*
Ito et al. (Plant Molecular Biology, 34:307-316, 1997).*
Kapadia et al. (Nitic Oxide, 20:279-288; 2009).*
McConnell et al. (Nature, 411:709-713, 2001).*
Hanzawa et al. (PNAS, 102:7748-7753, 2005).*
Wishart et al. (JBC, 270:26782-26785, 1995).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Nishimura et al. (Plant Cell Physiol., 41(5):583-590, 2000).*
Yang et al. (PNAS, 98:11438-11443, 2001).*
Li et al. (Nature Genetics. 47:827-832, Published May 18, 2015).*
Wang et al. (Plant Cell Physiol., 50:1721-1725, Published 2009).*

\* cited by examiner

*Primary Examiner* — Vinod Kumar
(74) *Attorney, Agent, or Firm* — Adam Warwick Bell; Matthew Rupert Kaser

(57) ABSTRACT

The present invention provides a new plant gene-rice high temperature resistance 1 gene (Rice High Temperature Resistance 1, HTR1) and encoded protein thereof. Also disclosed is the use of the high temperature resistance gene, especially for the enhancement of high-temperature resistance of plants in plant variety improvement and cross breeding.

8 Claims, 9 Drawing Sheets
Specification includes a Sequence Listing.

SEQUENCE LISTING

```
<160> NUMBER OF SEQ ID NOS: 30

<210> SEQ ID NO 1
<211> LENGTH: 708
<212> TYPE: DNA
<213> ORGANISM: Oryza glaberrima

<400> SEQUENCE: 1
atgggcgaca gccagtactc cttctccctc accaccttca gcccgtcggg gaagctggtg      60
cagatcgagc acgcgctgac ggcggtcggg tccggccaga cctccctcgg gatcaaagct     120
gctaatggag tagttattgc caccgagaag aagttgcctt ctattttagt ggatgaaaca     180
tctgtgcaaa agattcagtc gttgactcca aatattggtg tcgtctacag tggcatgggg     240
ccagacttcc gtgttttagt gaggaaaagt cgaaagcaag cacaacagta ttatcatctg     300
tacaaggaaa ctatacctgt tacacagcta gtccgagaaa ctgctgctgt catgcaggag     360
tttacacaat ctggtggtgt aagaccattt ggtgtatctt tgttgattgc tgggtatgat     420
gacaatggtc cccaattgta ccaggttgat ccatcagggt catacttctc ctggaaagca     480
tcagctatgg ggaaaaatgt gtcaaatgca aagacatttc ttgagaaaag atacacagaa     540
gacatggagc ttgacgatgc cattcatact gctattttaa ctctgaaaga aggatatgaa     600
ggacaaatct ccgccaacaa cattgaaatt gggataatcc gatctgaccg tgaattcaag     660
gttctgagcc ctgcagagat caaggatttc ttggaagagg tggaataa                 708

<210> SEQ ID NO 2
<211> LENGTH: 235
<212> TYPE: PRT
<213> ORGANISM: Oryza glaberrima

<400> SEQUENCE: 2
```

```
Met Gly Asp Ser Gln Tyr Ser Phe Ser Leu Thr Thr Phe Ser Pro Ser
1               5                   10                  15

Gly Lys Leu Val Gln Ile Glu His Ala Leu Thr Ala Val Gly Ser Gly
                20                  25                  30

Gln Thr Ser Leu Gly Ile Lys Ala Ala Asn Gly Val Val Ile Ala Thr
            35                  40                  45

Glu Lys Lys Leu Pro Ser Ile Leu Val Asp Glu Thr Ser Val Gln Lys
        50                  55                  60

Ile Gln Ser Leu Thr Pro Asn Ile Gly Val Val Tyr Ser Gly Met Gly
65                  70                  75                  80

Pro Asp Phe Arg Val Leu Val Arg Lys Ser Arg Lys Gln Ala Gln Gln
                85                  90                  95

Tyr Tyr His Leu Tyr Lys Glu Thr Ile Pro Val Thr Gln Leu Val Arg
            100                 105                 110

Glu Thr Ala Ala Val Met Gln Glu Phe Thr Gln Ser Gly Gly Val Arg
        115                 120                 125

Pro Phe Gly Val Ser Leu Leu Ile Ala Gly Tyr Asp Asp Asn Gly Pro
    130                 135                 140

Gln Leu Tyr Gln Val Asp Pro Ser Gly Ser Tyr Phe Ser Trp Lys Ala
145                 150                 155                 160

Ser Ala Met Gly Lys Asn Val Ser Asn Ala Lys Thr Phe Leu Glu Lys
                165                 170                 175

Arg Tyr Thr Glu Asp Met Glu Leu Asp Asp Ala Ile His Thr Ala Ile
            180                 185                 190

Leu Thr Leu Lys Glu Gly Tyr Glu Gly Gln Ile Ser Ala Asn Asn Ile
        195                 200                 205

Glu Ile Gly Ile Ile Arg Ser Asp Arg Glu Phe Lys Val Leu Ser Pro
    210                 215                 220

Ala Glu Ile Lys Asp Phe Leu Glu Glu Val Glu
225                 230                 235

<210> SEQ ID NO 3
<211> LENGTH: 708
<212> TYPE: DNA
<213> ORGANISM: Oryza sativa

<400> SEQUENCE: 3
atgggcgaca gccagtactc cttctccctc accaccttca gcccgtcggg gaagctggtg      60
cagatcgagc acgcgctgac ggcggtcggg tccggccaga cctccctcgg gatcaaagct     120
gctaatggag tagttattgc caccgagaag aagttgcctt ctattttagt ggatgaaaca     180
tctgtgcaaa agattcagtc gttgactcca aatattggtg ttgtctacag tggcatgggg     240
ccagacttcc gtgttttagt gaggaaaagt cgaaagcaag cacaacagta ttatcgtctg     300
tacaaggaaa ctatacctgt tacacagcta gtccgagaaa ctgctgctgt catgcaggag     360
tttacacaat ctggtggtgt aagaccattt ggtgtatctt tgttgattgc tgggtatgat     420
gacaatggtc cccaattgta ccaggttgat ccatcagggt catacttctc ctggaaagca     480
tcagctatgg ggaaaaatgt gtcaaatgca aagacatttc ttgagaaaag atacacagaa     540
gatatggagc ttgacgatgc cattcatact gctatttcaa ctctgaaaga aggatatgaa     600
ggacaaatct ccgccaacaa cattgaaatt gggataatcc gatctgaccg tgaattcaag     660
gttctgagcc ctgcagagat caaggatttc ttggaagagg tggaataa              708
```

```
<210> SEQ ID NO 4
<211> LENGTH: 235
<212> TYPE: PRT
<213> ORGANISM: Oryza sativa

<400> SEQUENCE: 4

Met Gly Asp Ser Gln Tyr Ser Phe Ser Leu Thr Thr Phe Ser Pro Ser
1               5                   10                  15

Gly Lys Leu Val Gln Ile Glu His Ala Leu Thr Ala Val Gly Ser Gly
            20                  25                  30

Gln Thr Ser Leu Gly Ile Lys Ala Ala Asn Gly Val Val Ile Ala Thr
        35                  40                  45

Glu Lys Lys Leu Pro Ser Ile Leu Val Asp Glu Thr Ser Val Gln Lys
    50                  55                  60

Ile Gln Ser Leu Thr Pro Asn Ile Gly Val Val Tyr Ser Gly Met Gly
65                  70                  75                  80

Pro Asp Phe Arg Val Leu Val Arg Lys Ser Arg Lys Gln Ala Gln Gln
                85                  90                  95

Tyr Tyr Arg Leu Tyr Lys Glu Thr Ile Pro Val Thr Gln Leu Val Arg
            100                 105                 110

Glu Thr Ala Ala Val Met Gln Glu Phe Thr Gln Ser Gly Gly Val Arg
        115                 120                 125

Pro Phe Gly Val Ser Leu Leu Ile Ala Gly Tyr Asp Asp Asn Gly Pro
    130                 135                 140

Gln Leu Tyr Gln Val Asp Pro Ser Gly Ser Tyr Phe Ser Trp Lys Ala
145                 150                 155                 160

Ser Ala Met Gly Lys Asn Val Ser Asn Ala Lys Thr Phe Leu Glu Lys
                165                 170                 175

Arg Tyr Thr Glu Asp Met Glu Leu Asp Asp Ala Ile His Thr Ala Ile
            180                 185                 190

Leu Thr Leu Lys Glu Gly Tyr Glu Gly Gln Ile Ser Ala Asn Asn Ile
        195                 200                 205

Glu Ile Gly Ile Ile Arg Ser Asp Arg Glu Phe Lys Val Leu Ser Pro
    210                 215                 220

Ala Glu Ile Lys Asp Phe Leu Glu Glu Val Glu
225                 230                 235

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
tgggttttga ggacttcc                                                       18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
cattgggaca tatgtagc                                                       18

<210> SEQ ID NO 7
<211> LENGTH: 18
```

```
<212> TYPE: DNA
<213> ORGANISM: Artificial Sequence
<220> FEATURE:
<223> OTHER INFORMATION: primer

<400> SEQUENCE: 7
ctggatacac agttgtcc                                                 18

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
aatcgatcga ttgtcccg                                                 18

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
cgacgacaag tacgatcg                                                 18

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
tgatctctcg atccacac                                                 18

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
aagcaatcgt agttagcaga                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tttggcaaga agtaaaacag                                               20

<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13
```
cgagctcatg ggcgacagcc agtactcctt ctccc                        35

<210> SEQ ID NO 14
<211> LENGTH: 78
<212> TYPE: DNA
<213> ORGANISM: Artificial Sequence
<220> FEATURE:
<223> OTHER INFORMATION: primer

<400> SEQUENCE: 14
gctctagact attatttgtc atcgtcatct ttgtagtccg ctgagcctcc tccttccacc    60
tcttccaaga aatccttg                                                 78

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
cggggtaccc agcagcagcc acagcaaa                                      28

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
agtgagacaa attattccac ctgcaggaga ttcagtttga                         40

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17
tgcaggtgga ataatttgtc tcactgctgc tgctacagcc                         40

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
ctcaggtcga aaaatttgtc tcattcctgc tgctaggctg                         40

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
aatgagacaa atttttcgac ctgagagagg caaaagtgaa                         40

<210> SEQ ID NO 20
<211> LENGTH: 29

<212> TYPE: DNA
<213> ORGANISM: Artificial Sequence
<220> FEATURE:
<223> OTHER INFORMATION: primer

<400> SEQUENCE: 20
cgcggatccg ctgctgatgc tgatgccat                                29

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
caatctggtg gtgtaagacc                                          20

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
tccaggagaa gtatgacc                                            18

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tccatcttgg catctctcag                                          20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gtaccctcat caggcatctg                                          20

<210> SEQ ID NO 25
<211> LENGTH: 36
<212> TYPE: DNA
<213> ORGANISM: Artificial Sequence
<220> FEATURE:
<223> OTHER INFORMATION: primer

<400> SEQUENCE: 25
cgggatccat gggcgacagc cagtactcct tctccc                        36

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26

```
gcgtcgactt attccacctc ttccaagaaa tccttg                                36
```

<210> SEQ ID NO 27
<211> LENGTH: 1909
<212> TYPE: DNA
<213> ORGANISM: Oryza glaberrima

<400> SEQUENCE: 27

```
tccagaggcc tgataagctt ggcttgaatc ttgaagagtg cacaccattt acagagcgac      60
ctttagagga aactggaaat attcattatg ttgctggtat tgaagatatt ggtcatctag     120
tgaatttcag attagaacat cttcgtcagg tacatacagc actgttccag taccaagtct     180
cttgcaaaac ttaattatgt taattatgtt tgatgtcttt gaatctgaca accccaacca     240
cttcatttgc aacagatgca atacatgcaa tattatgcac ctcatgcaaa tgtaccacct     300
tcagcagtac cagaaaacaa tgctgatgca actgaaaatg gcaatgctgg caatggtatg     360
cataaggcaa acgatggcat ggctgaagaa atggtgatg cagtgatgag aaataagatg      420
gaggaagata ctattgatac aatgcaggaa gaaaacaaga tggatggtaa aaatcctgag     480
gcaaacgaca tggctatgga ggagaagacc gtcgacggag atgatgatcc aaagaataag     540
atggaggaag gaaatactga ggcaaagaat aagatggagg aaggaaatac tgaggcaaag     600
gacaagatgg aggaagaaaa tgatgaggca agaacaata tggaagagtg agctaacatg      660
gctgttatct gattggacta gaggctaaca aaggcttcat gttcgctagc ttgatccacc     720
acaattcttg atctggaata ccaaatattg aagcacgcaa catcacatgg aggggttcat     780
aacatggctc ctgggatggt gtgcgtggaa tggagcatga tatgcgaagg ttaaagatat     840
ttttggagct tcttggccaa actatgctcc ttttatttcc ggccaattgt gtggtatacc     900
gtatacacat gtactgttat atggtttcac acatttggcc gaaacacacg acggctattc     960
aggggggcatt agcatgtaca aagagatga gtttcttgtt gtggtttctt cccttaactg    1020
tttaacatag ctatgcgagt gcaagagggc agatgaaaca ttgatgttgt gatatttttg    1080
tatactcgat tgttttgtaa tatggttacg aggagcgtta gagttttttt tttaacactg    1140
cagcatgagg aggtagacta ctgtaactgc tgtctgataa cactgcagaa actggtggta    1200
gctgtaagaa tggtgttcca agtttgaact aaatcaggtt ccaaaaatgt tgagctccg     1260
aaccaagcat gcagctcttg attatttata ctgcacggtt tgattcgagg tcgtggcttt    1320
gatcgttgtg ttgtgctttc cccacttcat ctagacgaga tcctcctggg attagaaagt    1380
gaccactcta gggtacatga aatcgtaaac aattcatcat tttagagtaa gtatgagatt    1440
tcatcatctt ttgtaatgtc atctcgaatt acctataggg gatttattct caaagataca    1500
ctaatgtgtc actgcccctt accaaaacat tgtcaccacc aaaacggagg tagtagcatt    1560
ttgaatccgt gacaagctac gaaactcgac ggcgactgcg attaggaaaa ggaagagagg    1620
atatgcaaaa aggactggga gtaggagtca catcggacgg cgcgcgatcc tcccggaacg    1680
aatcggacgg cccacgtgag tcgcgtagcc atggccccac atggcagacc gactccccct    1740
cttccctatt tctcctctat aatcccctca caagcaacaa cgaacgacac gcgagtcggc    1800
ggcgacaaca aatcgaaaat cgaacgggag aaattctctc tgattctctc tcgcgggcgg    1860
cggaagcagt cgtagttagc agaggccggc gagcgagccg ccgccggcg              1909
```

<210> SEQ ID NO 28
<211> LENGTH: 1912
<212> TYPE: DNA
<213> ORGANISM: Oryza sativa

<400> SEQUENCE: 28

```
tccagaggcc tgataagctt ggcttgaatc ttgaagagtg cacaccattt acagagcgac    60
ctttagagga aactggaaat attcattatg ttgctggtat tgaagatatt ggtcatctag   120
tgaatttcag attagaacat cttcgtcagg tacatacagc actgttccag taccaagtct   180
cttgcaaaac ttaattatgt taattatgtt tgatgtcttt gaatctgaca accccaacca   240
cttcatttgc aacagatgca atacatgcaa tattatgcac ctcatgcaaa tgtaccacct   300
tcagcagtac cagaaaacaa tgctgatgca actgaaaatg gcaatgctgg caatggtatg   360
cataaggcaa acgatgtcat ggctgaagaa atggtgatg cagtgatgag aaataagatg   420
gaggaagaca ctattgatac aatgcaggaa gaaaacaaga tggatggtaa aaatcctgag   480
gcaaacgaca tggctatgga ggagaagacc gtcgacggag atgatgatcc aaagaataag   540
atggaggaag gaaatactga ggcaaagaat aagatggagg aaggaaatac tgaggcaaag   600
gacaagatgg aggaagaaaa tgatgtgca aagaacaata tggaagagtg agctaacatg   660
gctgttatct gattggacta gaggctaaca aaggcttcat gttcgctagc ttgatccacc   720
acaattcttg atctggaata ccaaatattg aagcacgcaa catcacatgg aggggttcat   780
aacatggctc ctgggatggt gtgcgtggaa tggagcatga tatgcgaagg ttaaagatat   840
ttttggagct tcttggccaa actatgctcc ttttatttcc ggccaattgt gtggtatacc   900
gtatacacat gtactgttat atggtttcac acatttggcc gaaacacacg acggctattc   960
aggggcatt agcatgtaca aaagagatga gtttcttgtt gtggtttctt cccttaactg  1020
tttaacatag ctatgcgagt gcaagagggc agatgaaaca ttgatgttgt gatattttttg  1080
tatactcgat tgttttgtaa tatggttacg aggagcgtta gagtttttttt tttttttaaca  1140
ctgcagcatg aggaggtaga ctactgtaac tgctgtctga taacactgca gaaactggtg  1200
gtagctgtaa gaatggtgtt ccaagtttga actaaatcag gttccaaaaa tgtttgagct  1260
ccgaaccaag catgcagctc ttgattattt atactgcacg gtttgattcg aggtcgtggc  1320
tttgatcgtt gtgttgtgct ttccccactt catctagacg agatcctcct gggattagaa  1380
agtgaccact ctagagtaca tgaaatcgta acaattcat cattttagag taagtatgag  1440
atttcatcat cttttgtaat gtcatctcga attacctata ggggatttat tctcaaagat  1500
acactaatgt gtcactgccc cttaccaaaa cattgtcacc accaaaacgg aggtagtagc  1560
attttgaatc cgtgacaagc tacgaaactc gacggcgact gcgattagga aaggaagag  1620
aggatacca aaaggactg ggagtaggag tcacatcgga cggcgcgcga ccctcccgga  1680
acgaatcgga cggccacgt gagtcgcgta gccatggccc cacatggcag accgactccc  1740
cctcttccct atttctcctc tataatcccc tcacaagcaa caacgaacga cacgcgagtc  1800
ggcggcgaca acaaatcgaa aatcgaacgg gagaaattct ctctgattct ctctcgcggg  1860
cggcggaagc aatcgtagtt agcagaggcc ggcgagcgag ccgccaccgg cg          1912
```

<210> SEQ ID NO 29
<211> LENGTH: 6292
<212> TYPE: DNA
<213> ORGANISM: Oryza glaberrima

<400> SEQUENCE: 29

```
tccagaggcc tgataagctt ggcttgaatc ttgaagagtg cacaccattt acagagcgac    60
ctttagagga aactggaaat attcattatg ttgctggtat tgaagatatt ggtcatctag   120
```

```
tgaatttcag attagaacat cttcgtcagg tacatacagc actgttccag taccaagtct      180
cttgcaaaac ttaattatgt taattatgtt tgatgtcttt gaatctgaca accccaacca      240
cttcatttgc aacagatgca atacatgcaa tattatgcac ctcatgcaaa tgtaccacct      300
tcagcagtac cagaaaacaa tgctgatgca actgaaaatg gcaatgctgg caatggtatg      360
cataaggcaa acgatggcat ggctgaagaa atggtgatga cagtgatgag aaataagatg      420
gaggaagata ctattgatac aatgcaggaa gaaaacaaga tggatggtaa aaatcctgag      480
gcaaacgaca tggctatgga ggagaagacc gtcgacggag atgatgatcc aaagaataag      540
atggaggaag gaaatactga ggcaaagaat aagatggagg aaggaaatac tgaggcaaag      600
gacaagatgg aggaagaaaa tgatgaggca agaacaata tggaagagtg agctaacatg       660
gctgttatct gattggacta gaggctaaca aaggcttcat gttcgctagc ttgatccacc      720
acaattcttg atctggaata ccaaatattg aagcacgcaa catcacatgg aggggttcat      780
aacatggctc ctgggatggt gtgcgtggaa tggagcatga tatgcgaagg ttaaagatat      840
ttttggagct tcttggccaa actatgctcc ttttatttcc ggccaattgt gtggtatacc      900
gtatacacat gtactgttat atggtttcac acatttggcc gaaacacacg acggctattc      960 aggggggcatt agcatgtaca aaagagatga gtttcttgtt gtggtttctt cccttaactg     1020
tttaacatag ctatgcgagt gcaagagggc agatgaaaca ttgatgttgt gatatttttg     1080
tatactcgat tgttttgtaa tatggttacg aggagcgtta gagttttttt tttaacactg     1140
cagcatgagg aggtagacta ctgtaactgc tgtctgataa cactgcagaa actggtggta     1200
gctgtaagaa tggtgttcca agtttgaact aaatcaggtt ccaaaaatgt ttgagctccg     1260
aaccaagcat gcagctcttg attatttata ctgcacggtt tgattcgagg tcgtggcttt     1320
gatcgttgtg ttgtgctttc cccacttcat ctagacgaga tcctcctggg attagaaagt     1380
gaccactcta gggtacatga aatcgtaaac aattcatcat tttagagtaa gtatgagatt     1440
tcatcatctt ttgtaatgtc atctcgaatt acctataggg gatttattct caaagataca     1500
ctaatgtgtc actgccccct accaaaacat tgtcaccacc aaaacggagg tagtagcatt     1560
ttgaatccgt gacaagctac gaaactcgac ggcgactgcg attaggaaaa ggaagagagg     1620
atatgcaaaa aggactggga gtaggagtca catcggacgg cgcgcgatcc tcccggaacg     1680
aatcggacgg cccacgtgag tcgcgtagcc atggccccac atggcagacc gactccccct     1740
cttccctatt tctcctctat aatcccctca caagcaacaa cgaacgacac gcgagtcggc     1800
ggcgacaaca aatcgaaaat cgaacgggag aaattctctc tgattctctc tcgcgggcgg     1860
cggaagcagt cgtagttagc agaggccggc gagcgagccg ccgccggcga tgggcgacag     1920
ccagtactcc ttctcccctca ccaccttcag gtgcgctacc ctctctctct cttttccggc     1980
ggagatcggg agcatattgg tctctgacgc gctcgtgtgg cttccgttcc gctgctgcag     2040
cccgtcgggg aagctggtgc agatcgagca cgcgctgacg gcggtcgggt ccggccagac     2100
ctccctcggg atcaaaggtg cgtgccactc cctcccctt aatctccgat tagggatgat      2160
gcggatgagt tttttttttt tgttggtac agtggtacga ttgcggtcgt gggatttagg      2220
gtttaggtct tggcctcgtg tggattgtgg gagcgtgtgc gctggttcgt cgcagagggt     2280
gggtaggtta ggctgggggt tttggagccc ctggatgctt gtcgactctg ctattggcag     2340
ctagctgtgg tgaactggtg atatacattt ttttcggtg cctatgccgt attgggcaat      2400
gtgggcactt gtggaaaatt tgaaccaatg aagttgaaac gtttggcgaa gttggttgtt     2460
tattatttct gtgaagtaaa tggagattgt cagagtttgt agattgcaaa agtagaaatt     2520
```

```
ctatctataa tatgattatc taaagtacta aagaagttga tacttggtct gaagattgtg    2580
tcctttactt gcttagatga cctgctaaac aaatccacct aaaacaggag gaacacattt    2640
ctggaactat gcatgaccga tttgttgttt gtttctggct atgatgctac ctgagcttga    2700
tttttttttt ttacatagtt tttcaaagac aacatgtgca aatatgaata ctataggttg    2760
ggcttgagct gtctaggatg attaacacct tgcaaatata tctgcacagg catgaatgaa    2820
atctggaaaa tgataagttg agttcctatc aatgagttgt tcagtgtttt ataagtagca    2880
ctgtagccac atgcacgcac ctacacacaa gtgcctcttt gtatgcacaa attgcatggt    2940
ttccagtgtt catttgtttt tcaaaataat ctaactgtac ctggtctgga aaacaactac    3000
tatgcttggt tctgctcagc accaatttaa caactgaagg tgaactattg tctgagttga    3060
atgaaactat agtttggcaa atatttccta gacactaact tctaatactt ttagttgtcc    3120
gaataatttg caatgtgtgt tgtaggtgca tatttattag attcctccat tacacaggct    3180
aggtccataa aattgcttgg ttcctccaat gcaagcttaa taattttgca aaatatttgg    3240
tgttgtaaca gctgctaatg gagtagttat tgccaccgag aagaagttgc cttctatttt    3300
agtggatgaa acatctgtaa gtgtgacatt actcacaatt taagctccct tatctgttca    3360
tattctggag gcactaatga atactcatat tcatacataa aggtgcaaaa gattcagtcg    3420
ttgactccaa atattggtgt cgtctacagg tacttatttt aactgtgttt cattgttcat    3480
atactgctgt cttgctatgt acaaccttat tcattatctt acactttata ttacgctaca    3540
taatattgta ctgctatctt aatccctcta aaaaaattat tttcataatt tcttgatctt    3600
atatgtattc actgcccctt tgcactaaca agatggtata gaaacaacta gaaaggcatg    3660
agcacatgag acatttcatg tcttttgaga aaattatcgt gtacatacta tatatactag    3720
ggaaaaaaac atgcctacat catccttct gcctcatctt ataaagcatt gattctttta    3780
actaattttg ctagtgttaa tagttttgcaa gtttgatttg gtaatttagt tgactgttaa    3840
tattttcgaa ttacaacctg tgaatgcttc attttcatcc aataagaaca aaaaacagga    3900
attacattgg ttcttattct agtgatttga acgttagaac tcgggcttat tcttctcttg    3960
aaatgcttat tacaagtgcc aacttcttgt tgctgaggct caatcatgtt agacactggc    4020
ctttggttag attaatgact aggatggtcg actctcacta ctttgttgca tatattcatg    4080
tgcttacctt gtttttttt cttccagtgg catggggcca gacttccgtg ttttagtgag    4140
gaaaagtcga aagcaagcac aacagtatta tcatctgtac aaggtatttg atggtctatt    4200
ttgcagtttt acagtgctat cctaaaaaaa tatgtcgtag acgtaggaat agtctttcag    4260
aagggattta cattgtcagt aaaataaagt gattccgaat cagtgtttct gctttctaac    4320
tgtattgtct atatataaat gcaggaaact atacctgtta cacagctagt ccagaaaact    4380
gctgctgtca tgcaggagtt tacacaatct gggtatgtaa aatttgtaca agcagattga    4440
taaaccatga acattctctg ccttatctat tcagaagaat taagctgtca ttttttatac    4500
acaaacagca tgttctagaa tgttaacaca atgcttgttt cttatcaatg taatgcatat    4560
tctttcacaa actagtaaga atataagacc ccagtggtcc acgtggtcaa atgaaaacca    4620
tggtcggtga agtacaaaag ccagaatatc tattttatta cttgtagatt tgtatataat    4680
aaatttcatt atggcttttt tgcagtggtg taagaccatt tggtgtatct ttgttgattg    4740
ctgggtatga tgcaatggt ccccaattgt accaggtatt gacaaataat tatatacaac    4800
agagaaggtt ttgtgtaaat acaaagtgtc aaatgcgaac aatctttctt tctttttttc    4860
```

```
ttgcttcaga ccattgcatt tacgactttg tagttattaa tattgcagac agttgacatt        4920
gtcattgttt tattaggttg atccatcagg gtcatacttc tcctggaaag catcagctat        4980
ggggaaaaat gtgtcaaatg caaagacatt tcttgagaaa aggtaagaag attgacaaaa        5040
cttacaattg atagtagata ctgttacatg tggtatcatt tttcttccat ttgatcataa        5100
acatggtgct taattctatg ctacatatct ccttttctta atttaagtgt caagtttata        5160
caggttcatg ccccccccc cccccccaaa aaaaaaagg catgaatgca ttaatttcat         5220
attcatttat tgtttcattg cagatacaca aaagacatga agcttgacga tgccattcat        5280
actgctattt taactctgaa agaagggtac ctcactatta ttgtgtgttg attctgttta        5340
ccactttcct ttttaaaaac aacttgatgg attacaaact tgcagatatg aaggacaaat        5400
ctccgccaac aacattgaaa ttgggataat ccgatctgac cgtgaattca agtatgatac        5460
agacttaatc aacttgttgc taccatttat cagatttcat attctgttat ctctgccaaa        5520
gatctaaatc ttttagcttt tctaaattgt ggatttctag aaaatagcca tctgttttgc        5580
atcataggcg tctttatctt aaaaaactgc acatttaccc ccatctgagt agaggctcat        5640
aataggttaa atcttttctg gagaataatc ctagatttct ttcgtccttt ccatttgatg        5700
tttttttttt ttaactaagg tgtagtattt tgttatcacg ctagtctctg gtatagctgt        5760
ctattctgcc caaactattt gagatgatag aacatgttgc atcgttgccc tcagatggtt        5820
tgctgactgt taatatttc ctgaaaaata cagggttctg agccctgcag agatcaagga        5880
tttcttggaa gaggtggaat aatttgtctc aacaatctca tgtttcaaac cagtggacac        5940
ctgagcagct gcctcgaagt tatatcccct ttcattcatg aactgattgg caccagtgac        6000
acgagacaaa tgtttattca gattctcatg aatgaaaatg tgtttttagg aacgtatttg        6060
atttggcacg gtgtcttctg tatcctcttg tgcccatcct agtctcctcg gccagtgcta        6120
caactatttg gcgtctcctt acttttgtag tctgttttac ttcttgccaa atgaagcaca        6180
tgccatcttt tgctcttgca agtgtagttt gctccctgga ttgttaggac ttggaagccc        6240
acccagttgt tgcagctgtt acactggtgg tggtaaatcg ctgtctggtg ta              6292
```

<210> SEQ ID NO 30
<211> LENGTH: 6289
<212> TYPE: DNA
<213> ORGANISM: Oryza sativa

<400> SEQUENCE: 30

```
tccagaggcc tgataagctt ggcttgaatc ttgaagagtg cacaccattt acagagcgac          60
ctttagagga aactggaaat attcattatg ttgctggtat tgaagatatt ggtcatctag         120
tgaatttcag attagaacat cttcgtcagg tacatacagc actgttccag taccaagtct         180
cttgcaaaac ttaattatgt taattatgtt tgatgtcttt gaatctgaca accccaacca         240
cttcatttgc aacagatgca atacatgcaa tattatgcac ctcatgcaaa tgtaccacct         300
tcagcagtac cagaaaacaa tgctgatgca actgaaaatg gcaatgctgg caatggtatg         360
cataaggcaa acgatgtcat ggctgaagaa aatggtgatg cagtgatgag aaataagatg         420
gaggaagaca ctattgatac aatgcaggaa gaaacaagaa tggatggtaa aaatcctgag         480
gcaaacgaca tggctatgga ggagaagacc gtcgacggag atgatgatcc aaagaataag         540
atggaggaag gaaatactga ggcaaagaat aagatggagg aaggaaatac tgaggcaaag         600
gacaagatgg aggaagaaaa tgatgtgca agaacaata tggaagagtg agctaacatg          660
gctgttatct gattggacta gaggctaaca aaggcttcat gttcgctagc ttgatccacc         720
```

```
acaattcttg atctggaata ccaaatattg aagcacgcaa catcacatgg aggggttcat      780
aacatggctc ctgggatggt gtgcgtggaa tggagcatga tatgcgaagg ttaaagatat      840
ttttggagct tcttggccaa actatgctcc ttttatttcc ggccaattgt gtggtatacc      900
gtatacacat gtactgttat atggtttcac acatttggcc gaaacacacg acggctattc      960 aggggggcatt agcatgtaca aaagagatga gtttcttgtt gtggtttctt cccttaactg     1020
tttaacatag ctatgcgagt gcaagagggc agatgaaaca ttgatgttgt gatattttg      1080 tatactcgat tgttttgtaa tatggttacg aggagcgtta gagttttttt tttttaaca      1140 ctgcagcatg aggaggtaga ctactgtaac tgctgtctga taacactgca gaaactggtg     1200
gtagctgtaa gaatggtgtt ccaagtttga actaaatcag gttccaaaaa tgtttgagct     1260
ccgaaccaag catgcagctc ttgattattt atactgcacg gtttgattcg aggtcgtggc     1320
tttgatcgtt gtgttgtgct ttccccactt catctagacg agatcctcct gggattagaa     1380
agtgaccact ctagagtaca tgaaatcgta aacaattcat cattttagag taagtatgag     1440
atttcatcat cttttgtaat gtcatctcga attacctata ggggatttat tctcaaagat     1500
acactaatgt gtcactgccc cttaccaaaa cattgtcacc accaaaacgg aggtagtagc     1560
attttgaatc cgtgacaagc tacgaaactc gacggcgact gcgattagga aaggaagag     1620 aggataccca aaaaggactg ggagtaggag tcacatcgga cggcgcgcga ccctcccgga     1680
acgaatcgga cggcccacgt gagtcgcgta gccatggccc cacatggcag accgactccc     1740
cctcttccct atttctcctc tataatcccc tcacaagcaa caacgaacga cacgcgagtc     1800
ggcggcgaca acaaatcgaa aatcgaacgg gagaaattct ctctgattct ctctcgcggg     1860
cggcggaagc aatcgtagtt agcagaggcc ggcgagcgag ccgccaccgg cgatgggcga     1920
cagccagtac tccttctccc tcaccacctt caggtgcgct accctctctc tctctttttcc    1980 ggcggagatc gggagcatat tggtctctga cgcgctcgtg tggcttccgt tccgctgctg     2040
cagcccgtcg gggaagctgg tgcagatcga gcacgcgctg acggcggtcg ggtccggcca     2100
gacctccctc gggatcaaag gtgcgtgcca ctccctcccc tttaatctcc gattagggat     2160
tatgcggatg agttttttt tttgttggta cagtggtacg attgcggtcg tgggatttag      2220
ggtttaggtc ttggcctcgt gtggattgtg ggagcgtgtg cgctggttcg tcgcagaggg     2280
tgggtaggtt aggctggggg ttttggagcc cctggatgct tgtcgactct gctattggca     2340
gctagctgtg gtgaactggt gatatacatt ttttttcggt gcctatgccg tattgggcaa     2400
tgtgggcact tgtggaaaat ttgaaccaat gaagttgaaa cgtttggcga agttggttgt     2460
ttattatttc tgtgaagtaa atggagattg tcagagtttg tagattgcaa agtagaaat      2520 tctatctata atatgattat ctaaagtact aaagaagttg atacttggtc tgaagattgt     2580
gtcctttact tgcttagatg acctgctaaa caaatccacc taaaacagga ggaacacatt     2640
tctgaaacta tgcatgaccg atttgttgtt tgtttctggc tatgatgcta cctgagcttg     2700 atttttttt tacatagttt ttcaaagaca acatgtgcaa atatgaatac tataggttgg     2760
gcttgagctg tctaggatga ttaacaccctt gcaaatatat ctgcacaggc atgaatgaaa    2820
tctgaaaaat gataagttga gttcctatca atgagttgtt cagtgtttta taagtagcac     2880
tgtagccaca tgcacgcacc tacacacaag tgcctctttg tatgcacaaa ttgcatggtt     2940
tccagtgttc atttgttttt caaaataatc taactgtacc tggtctggaa aacaactact     3000
atgcttggtt ctgctcagca ccaatttaac aactgaaggt gtactattgt ctgagttgaa     3060
```

```
tgaaactata gtttggcaaa tatttcctag acactaactt ctaatacttt tagttgtccg    3120
aataatttgc aatgtgtgtt gtaggtgcat atttattaga ttcctccatt acacaggcta    3180
ggtccataaa attgcttggt tcctccaatg caagcttaat aattttgcaa atatttggt    3240 gttgtaacag ctgctaatgg agtagttatt gccaccgaga agaagttgcc ttctatttta    3300
gtggatgaaa catctgtaag tgtgacatta ctcacaattt aagctcccctt atctgttcat    3360 attctggagg cactaatgaa tactcatatt catacataaa ggtgcaaaag attcagtcgt    3420
tgactccaaa tattggtgtt gtctacaggt acttatttta actgtgtttc attgttcata    3480
tactgctgtc ttgctatgta caaccttatt cattatctta cactttatat tacgctacat    3540
aatattgtac tgctatctta atccctctaa aaaaattatt ttcataattt cttgatctta    3600
tatgtattca ctgccccttt gcactaacaa gatggtatag aaacaactag aaaggcatga    3660
gcacatgaga catttcatgt cttttgagaa aattatcgtg tacatactat atatactagg    3720
gaaaaaaaca tgcctacatc ataccttctg cctcatctta taaagcattg attcttttaa    3780
ctaattttgc tagtgttaat agtttgcaag tttgatttgg taatttagtt gactgttaat    3840
attttcgaat tacaacctgt gaatgcttca ttttcatcca ataagaacaa aaaacaggaa    3900
ttacattggt tcttattcta gtgatttgaa cgttagaact cgggcttatt cttctcttga    3960
aatgcttatt acaagtgcca acttcttgtt gctgaggctc aatcatgtta gacactggcc    4020
tttggttaga ttaatgacta ggatggtcga ctctcactac tttgttgcat atattcatgt    4080
gcttaccttg ttttttttttt cttccagtgg catggggcca gacttccgtg ttttagtgag    4140
gaaaagtcga aagcaagcac aacagtatta tcgtctgtac aaggtatttg atggtctatt    4200 ttgcagttttt acagtgctat cctaaaaaaa tatgtcgtag acgtaggaat agtctttcag    4260
aagggattta cattgtcagt aaaataaagt gattccgaat cggtgtttct gctttctaac    4320
tgtattgtct atatataaat gcaggaaact atacctgtta cacagctagt ccgagaaact    4380
gctgctgtca tgcaggagtt tacacaatct gggtatgtaa aatttgtaca agcagattga    4440
taaaccatga acattctctg ccttacctat tcagaagaat taagctgtca ttttttatac    4500
acaaacagca tgttctagaa agttaacaca atgcttgttt cttatcaatg taatgcatat    4560
tctttcacaa actagtaaga atataagacc ccagtggtcc acgtggtcaa atgaaaacca    4620
tggtcggtga agtacaaaag ccagaatatc tattttatta cttgtagatt tgtatataat    4680
aaatttcatt atggcttttt tgcagtggtg taagaccatt tggtgtatct tgttgattg    4740 ctgggtatga tgacaatggt ccccaattgt accaggtatt gacaaataat tatatacaac    4800
agagaaggtt ttgtgtaaat acaaagtgtc aaatgcgaac aatctttctt tcttttttttc    4860 ttgcttcaga ccattgcatt tacgactttg tagttattaa tattgcagac agttgacatt    4920
gtcattgttt tattaggttg atccatcagg gtcatacttc tcctggaaag catcagctat    4980
ggggaaaaat gtgtcaaatg caaagacatt tcttgagaaa aggtaagcag attgacaaaa    5040
cttacaattg atactagata ctgttacatg tggtatcatt tttcttccat ttgatcataa    5100
acatggtgct taattctatg ctacatatct ccttttctta atttaagtgt caagtttata    5160
caggctcatg ccccccccccc cccaaaaaaa aagaaggcat gaatgcatta atttcatatt    5220
catttattgt ttcattgcag atacacagaa gatatggagc ttgacgatgc cattcatact    5280 gctatttttaa ctctgaaaga agggtacctc actattattg tgtgttgatt tgtttaccac    5340
ttctttcctt tttaaaaaca acttgatgga ttacaaactt gcagatatga aggacaaatc    5400
tccgccaaca acattgaaat tgggataatc cgatctgacc gtgaattcaa gtatgataca    5460
```

-continued

```
gacttaatca acttgttgct accatttatc agatttcata ttctgttatc tctgccaaag    5520
atctaaatct tttagctttt ctaaattgtg gatttctaga aaatagccat ctgttttgca    5580
tcataggcgt ctttatctta aaaaactgca catttacccc catctgagta gaggctcata    5640
ataggttaaa tcttttctgg agaataatcc tagatttctt tcgtcctttc catttgatgt    5700
ttttttttta actaaggtgt agtattttgt tatcacgcta gtctctggta tagctgtcta    5760
ttctgtccaa actatttgag atgatagaac atgttgcatc gttgccctca gatggtttgc    5820
tgactgttaa tattttcctg aaaaatacag ggttctgagc cctgcagaga tcaaggattt    5880
cttggaagag gtggaataat ttgtctcaac aatctcatgt ttcaaaccag tggacacctg    5940
agcagctgcc tcgaagttat atcccctttc attcatgaac tgattggcac cagtgacacg    6000
agacaaatgt ttattcagat tctcatgaat gaaaatgtgt ttttaggaac gtatttgatt    6060
tggcacggtg tcttctgtat cctcttgtgc ccatcctagt ctcctcggcc agtgctacaa    6120
ctatttggcg tctccttact tttgtagtct gttttacttc ttgccaaatg aagcacatgc    6180
catcttttgc tcttgcaagt gtagtttgct ccctggattg ctaggacttg gaagcccacc    6240
cagttgttgc agctgttaca ctggtggtgg taaatcgctg tctggtgta               6289
```

RICE HIGH TEMPERATURE RESISTANCE GENE AND USE IN CROP BREEDING RESISTANCE TO HIGH TEMPERATURE THEREOF

TECHNICAL FIELD

The invention relates to the field of botany, in particular, the present invention relates to a new rice (*Oryza sativa*) high temperature resistance gene and an encoded protein thereof. The present invention also discloses a use of a gene encoding such a high temperature resistance protein, and in particular use in the alteration of the high temperature resistance of plants in the plant breed improvement and crossbreeding.

A sequence listing text (.txt) file is submitted herewith under 37 CFR. 1.821(c) and is hereby incorporated by reference in its entirely. The details of the file as required under 37 CFR. 1.52(e)(5) and 37 CFR 1.77(b)(5) are as follows: Name of file is XU_P2017-0347_New_seq_List_P2017-0347; date of creation is Thursday, Aug. 10, 2017, 2:47:20 AM; size is 31.5 KB. The content of the sequence listing information recorded in computer readable form is identical to the written sequence listing (if any) and identical to the sequence information provided with the original filed application and with the priority application, and contains no new matter.

BACKGROUND

In recent years, the global climate has greatly changed, the frequency of extreme hot weather has become larger, resulting in the reduction of a large number of food crops, and making a great impact on the production and life.

Studies have shown that high temperatures will be the most important environmental factors threatening global food security: for example, high temperatures have become a major contributor to the threat of wheat production in Europe (wheat is very sensitive to high temperatures during grain filling), instead of drought; and the production of rice, maize and other major food crops is also seriously affected by high temperature in recent 30 years.

In China, high temperature has caused great loss to the rice yield. Especially in the south of Yangtze River, double-season early rice flowering and filling period, early blooming period of early rice to heading flowering stage, and early-maturing *Japonica* Rice flowering and grain filling stage in the middle and lower reaches of Yangtze River, are usually in the hot summer season, therefore high temperature stress results in that the rice can not normally loose powder, fertilization, and grain filling is not full, thereby greatly reducing the rice yield and its quality.

It is an important measure to deal with the high temperature damage on rice by understanding the high temperature resistance mechanism of rice from the genetic aspects, and applying genetic engineering means to cultivate high quality rice varieties with good high temperature resistance. It is of great significance to promote the continuous and steady development of rice production, and meantime, research on high temperature resistance genes in rice and the mechanism of its action will also provide the genetic resources and reference for high-temperature breeding of other crops.

However, the mechanism of the resistance of plant to high temperature is still unknown. Therefore, in order to change the high temperature resistance of plant varieties effectively and specifically, there is an urgent need in the art for the development of proteins and coding genes thereof associated with high temperature resistance.

SUMMARY OF THE INVENTION

The object of the invention is to provide a new high temperature resistance gene (i.e., rice high temperature resistance protein 1 gene) and fragments, analogues and derivatives thereof.

Another object of the invention is to provide polynucleotides encoding such polypeptides.

Another object of the invention is to provide a method for producing these polypeptides and a use of the polypeptide and encoding sequence, in particular, in aspects, such as the alteration of plant resistance to high temperatures.

In the first aspect of the present invention, a new isolated rice high temperature resistance protein 1 (abbreviated as HTR1) is provided, which is derived from rice. The rice high temperature resistance protein 1 is $\alpha 2$ subunit of 26S proteasome in rice and the amino acid in the $\alpha 2$ subunit corresponding to position 99 of the $\alpha 2$ subunit in Asian cultivated rice (e.g., SEQ ID NO.: 4) is mutated from Arg to His;

or the rice high temperature resistance protein 1 is a polypeptide having the amino acid sequence of SEQ ID NO: 2, an active fragment, or a conservative variant polypeptide thereof.

In another preferred embodiment, the rice high temperature resistance protein 1 is derived from African rice (CG14).

In another preferred embodiment, the polypeptide is selected from the group consisting of:

(a) a polypeptide having the amino acid sequence of SEQ ID NO: 2;

(b) a polypeptide derived from (a), wherein the polypeptide is obtained through substitution, deletion or addition of one or more amino acid residues of SEQ ID NO.:2 and has the function of improving the resistance to high temperature of the rice.

In another preferred embodiment, the amino acid of the derivatized polypeptide at a position corresponding to position 99 in SEQ ID NO.:2 is His.

In another preferred embodiment, the high temperature resistant protein 1 has one or more characteristics selected from the group consisting of:

(i) after degradation and denaturation under high temperature, the activity of protein is significantly higher than that of the protein shown in SEQ ID NO: 4;

(ii) under high temperature, the stability of the protein itself is significantly higher than that of the protein shown in SEQ ID NO: 4.

In anther preferred embodiment, the expression, "significantly higher" means satisfying the following formula:

$$A1/A0 \geq 2$$

wherein A1 is the activity, after degradation and denaturation under high temperature, of rice high temperature resistance protein 1;

while, A0 is the activity, after degradation and denaturation under high temperature, of the protein shown in SEQ ID NO.:4.

In another preferred embodiment, $A1/A0 \geq 3$, or $\geq 5$.

In another preferred embodiment, the high temperature indicates a temperature of 35-45° C., preferably 37-42° C., more preferably 39-42° C.

In the second aspect of the present invention, an isolated polynucleotide is provided, wherein the polynucleotide comprises a nucleotide sequence encoding the polypeptide according to the first aspect of the present invention;

or the polynucleotide is a promoter sequence specifically responsive to high temperature that drives the polypeptide according to the first aspect of the present invention in rice.

In another preferred embodiment, the polynucleotide encodes a polypeptide having the amino acid sequence shown in SEQ ID NO: 2.

In another preferred embodiment, the polynucleotide further comprises a promoter operably linked to the ORF sequence of the rice high temperature resistance protein 1.

In another preferred embodiment, the promoter is selected from the group consisting of: a constitutive promoter, a tissue-specific promoter, an inducible promoter, or a strong promoter.

In another preferred embodiment, the promoter is a promoter specifically responsive to high temperature; preferably, the sequence of the promoter is shown in SEQ ID NO.:27 and 28; more preferably, the polynucleotide sequence is selected from the group consisting of:

(a) a polynucleotide sequence having positions 1-708 in SEQ ID NO.:1;

(b) a polynucleotide sequence having positions 1-705 in SEQ ID NO.:1;

(c) a polynucleotide sequence having positions 1-6292 in SEQ ID NO.:29;

(d) a polynucleotide sequence shown in SEQ ID NO:27 or 28.

In another preferred embodiment, the polynucleotide is genomic sequence or cDNA sequence.

In the third aspect of the present invention, a vector is provided, wherein the vector comprises the polynucleotide according to the second aspect of the present invention.

In the fourth aspect of the present invention, a genetically engineered host cell is provided, wherein the host cell comprises the vector according to the third aspect of the present invention, or the polynucleotide according to the third aspect of the present invention is integrated into the genome of the host cell.

In another preferred embodiment, the host cell is selected from the group consisting of: plant cells, prokaryotic cells, yeast cells.

In another preferred embodiment, the host cell is a crop cell, including a gramineous plant cell, such as a rice cell.

In the fifth aspect of the present invention, a method for preparing a rice high temperature resistance protein 1 is provided, comprising:

(a) under conditions suitable for expression, culturing the host cell according to the fourth aspect of the present invention;

(b) isolating the rice high temperature resistance protein 1 from the culture.

In the sixth aspect of the present invention, a 26S proteasome is provided, wherein the α2 subunit contained in the 26S proteasome is the high temperature resistance polypeptide according to the first aspect of the present invention.

In the seventh aspect of the present invention, a method for improving a plant is provided, comprising steps of:

(1) providing a *Agrobacterium tumefacien* containing an expression vector, wherein the expression vector contains an encoding sequence of a rice high temperature resistant protein, and the rice high temperature resistance protein is the high temperature resistance polypeptide as in claim 1 or the polypeptide shown in SEQ ID NO.:4;

(2) contacting a plant cell or tissue or organ with the *Agrobacterium tumefacien* in step (1), thereby the DNA encoding sequence of the rice high temperature resistance protein being transferred into the plant cell and integrated into the chromosome of the plant cell;

(3) selecting the plant cell or tissue or organ into which the DNA encoding sequence of the rice high temperature resistance protein is transferred; and (4) regenerating the plant cell or tissue or organ in step (3) into a plant; and preferably, the method improves the high temperature resistance of the plant.

In another preferred embodiment, the plant comprises crops, forestry plant, vegetables, fruits, flowers, pastures (including turfgrass); preferably, comprises gramineous, leguminous and cruciferous plants; and more preferably, comprises rice, maize, sorghum, wheat, soybean or *Arabidopsis*.

In another preferred embodiment, the plant comprises: rice, wheat, maize, sorghum, cabbage and other cruciferous and other vegetables.

In another preferred embodiment, after step (4), the step of testing the high temperature resistant property of the plant is further comprised.

In another preferred embodiment, the method improves the high temperature resistant property of a plant.

In the eighth aspect of the present invention, a method for cultivating a high temperature resistant line of a plant is provided, comprising the steps of: improving the expression or activity of 26S proteasomes in the plant.

In another preferred embodiment, the α2 subunit in the 26S proteasomes is the high temperature resistant polypeptide according to the first aspect of the present invention.

In another preferred embodiment, the high temperature resistant polypeptide is operably linked to a promoter specifically responsive to high temperature.

In another preferred embodiment, "improving" comprises: increasing the expression level of the 26S proteasome-encoding gene and/or enhancing the activity of the 26S proteasome.

In the ninth aspect of the present invention, a use of the high temperature resistance polypeptide according to the first aspect of the present invention or encoding gene thereof, or the polypeptide shown in SEQ ID NO.:4 or encoding gene thereof for cultivating high temperature resistant lines of a plant, or for the preparation of a reagent or a kit for cultivating high temperature resistant lines of a plant.

In the tenth aspect of the present invention, an antibody that specifically binds to the rice high temperature resistance protein 1 as described above is provided. A nucleic acid molecule is further provided that can be used for detection, containing about 15-1500 nucleotides in the above polynucleotides in succession, which can be used as primers or probes (see Examples 2 and 3).

In the eleventh aspect of the present invention, an antibody against the protein of the present invention and a method for detecting the presence of the rice high temperature resistance protein 1 in a detection sample are provided, comprising: contacting the sample with the antibody specific to the rice high temperature resistance protein 1, observing whether an antibody complex is formed, and if the antibody complex is formed, it indicates the presence of the rice high temperature resistance protein 1 in the sample.

In the twelfth aspect of the present invention, a promotor sequence specifically responsive to high temperature and use thereof are provided, wherein the promotor is a promoter specifically responsive to high temperature that drives the polypeptide (HTR1) according to the present invention in rice, and preferably, the promoter sequence has a nucleotide sequence shown in SEQ ID NO.:27 or 28.

It should be understood that, within the scope of the present invention, the technical features specifically described above and below (such as the Examples) can be combined with each other, thereby constituting a new or preferred technical solution which needs not be described one by one.

Wherein, 2A shows that NIL(CG14) demonstrates a stronger high temperature resistance both at seedling stage and adult stage.

2B shows that under the normal growth condition, the yield of NIL (CG14) was not different from that of control NIL (WYJ).

2C shows that, under high temperature stress, the yield of NIL (CG14) was significantly higher than that of the control (the yield per plant was about 5 times higher than that of the control) during the flowering period.

2D shows that, under the high temperature stress, the yield of NIL (CG14) was significantly higher than that of the control during filling period. CK, normal growth conditions; HT, high temperature treatment.

Figure 3:
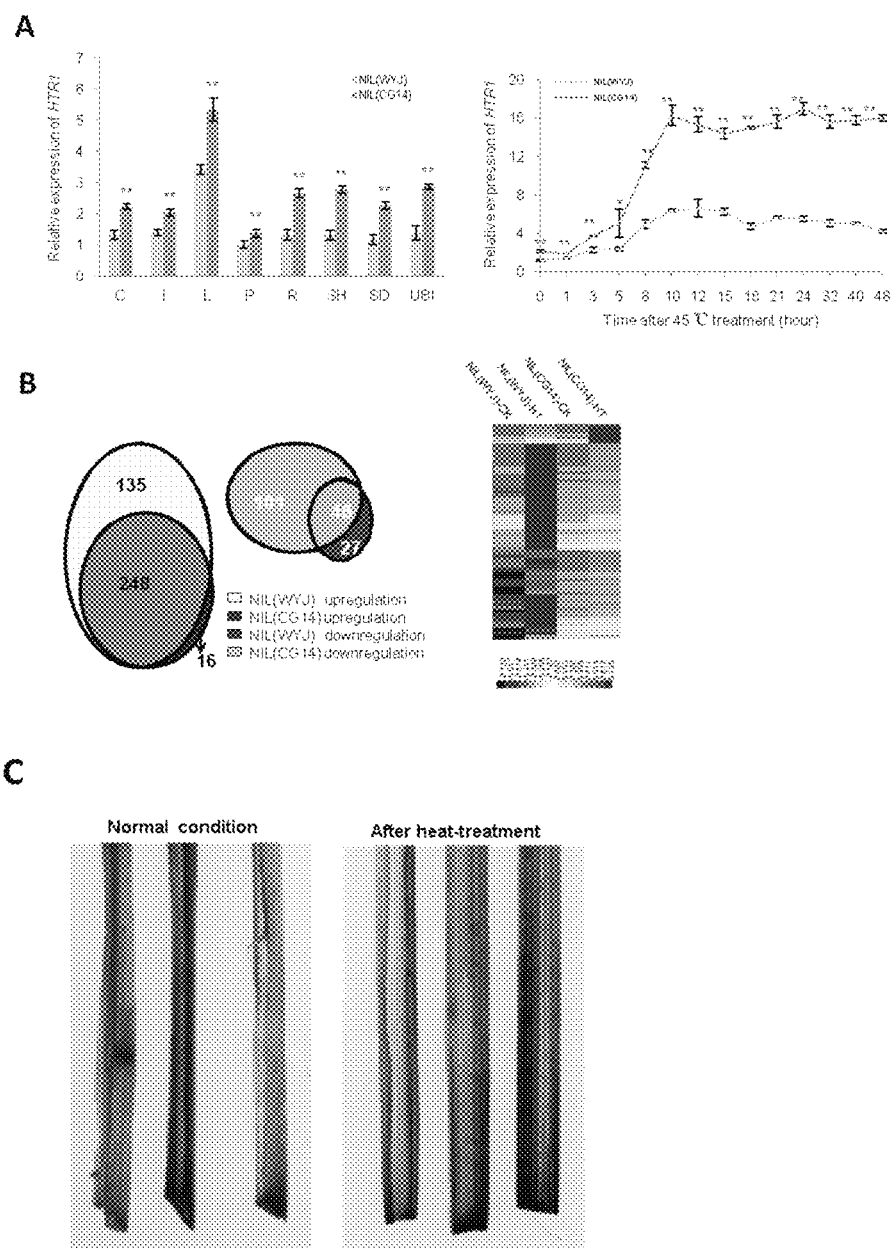

FIG. 3 shows high temperature response mechanism of HTR1.

Wherein, 3A shows that, HTR1 is ubiquitously expressed throughout each tissue and is expressed under high temperature induction; and the expression of HTR1$^{CG14}$ is higher than that of HTR1$^{WYJ}$ before and after induction. Wherein, C represents stem, I represents nodes, L represents leaves, P represents spike, R represents root, SH represents leaf sheath, SD represents seedling, and UBI represents unelongated basal internode.

3B shows that high-temperature treatment will accumulate ubiquitinated and denatured proteins, however, the ubiquitinated proteins accumulated in NIL (CG14) are significantly lower than the control NIL (WYJ), regardless of type or level. CK, before high temperature treatment; HT, 30 hours after high temperature treatment.

3C shows that the promoter of HTR1$^{CG14}$ is significantly induced by high temperature. High temperature treatment can significantly enhance the expression of GUS gene drived by the promoter.

Figure 4:
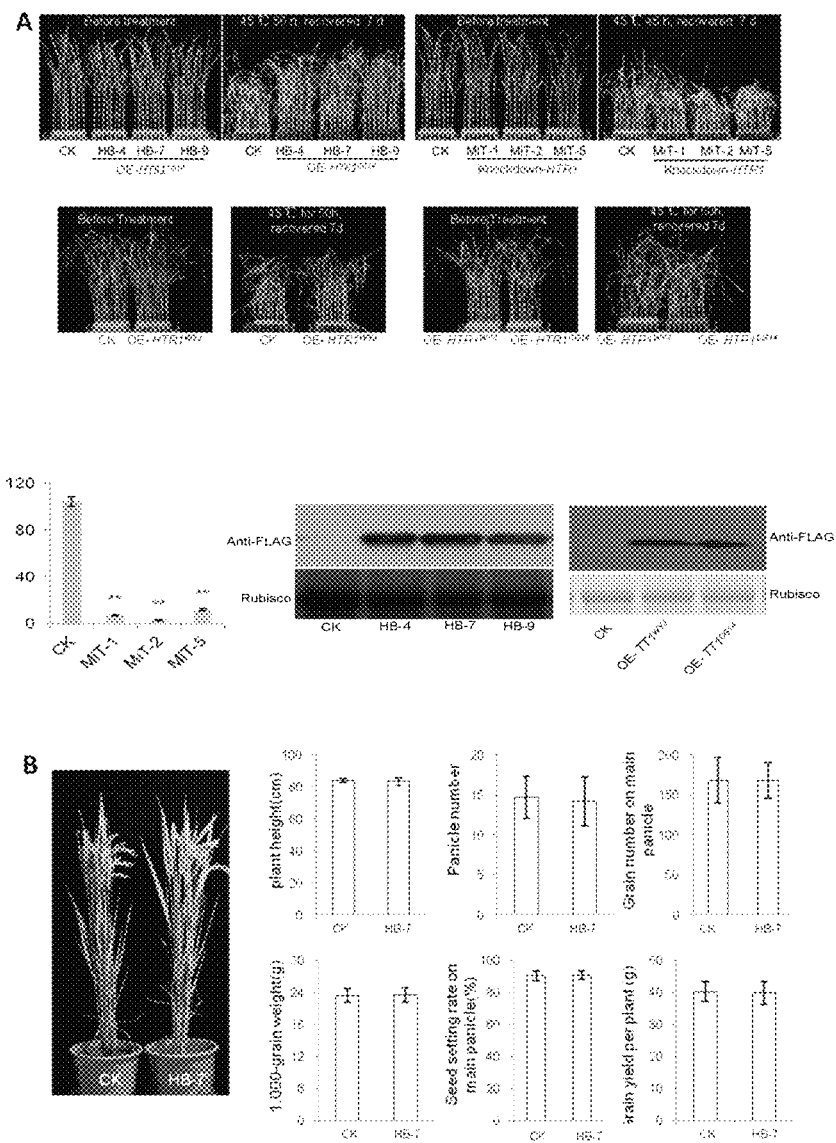
Figure 4:
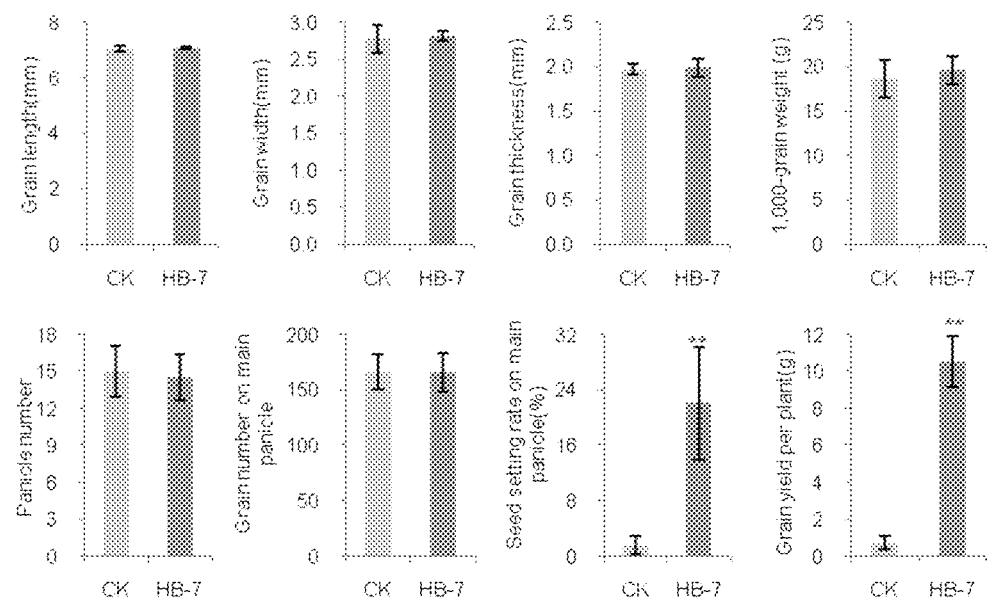
Figure 4:
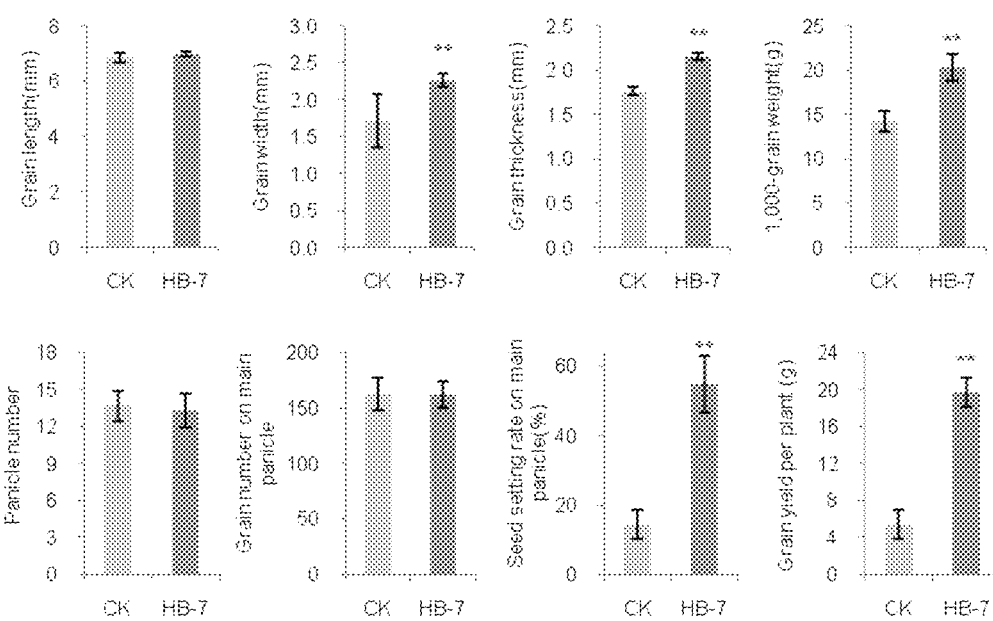

FIG. 4 shows that overexpression of HTR1$^{CG14}$ can significantly enhance the high temperature resistance of rice.

Wherein 4A shows that overexpression of HTR1$^{CG14}$ and HTR1$^{WYJ}$ can both enhance the high temperature resistance of rice, but the former has a stronger high temperature resistance; knockdown of HTR1$^{CG14}$ in NIL (CG14) will make rice sensitive to high temperature. The above two lines are the growth status of the corresponding rice lines before and after the high temperature treatment, and the following line is the expression level of HTR1 in the corresponding lines (the data shown for Knockdown line is real-time PCR data, while the overexpression line is detected for the expression of exogenous protein by western-blotting).

4B shows that, under normal growth conditions, the yield of transgenic rice with HTR1$^{CG14}$ overexpression is not different from that of the control. Wherein CK, transgenic negative control; HB-7, positive transgenic lines with HTR1$^{CG14}$ overexpression.

4C shows that, under high temperature stress, the yield of transgenic rice with HTR1$^{CG14}$ overexpression is higher than that of the control during the flowering period (the yield per plant is about 12 times higher than that of the control).

4D shows that, under high temperature stress, the yield of transgenic rice with HTR1$^{CG14}$ overexpression is higher than that of the control during the grain filling stage. Wherein CK, transgenic negative control; HB-7, positive transgenic lines with HTR1$^{CG14}$ overexpression.

Figure 5:
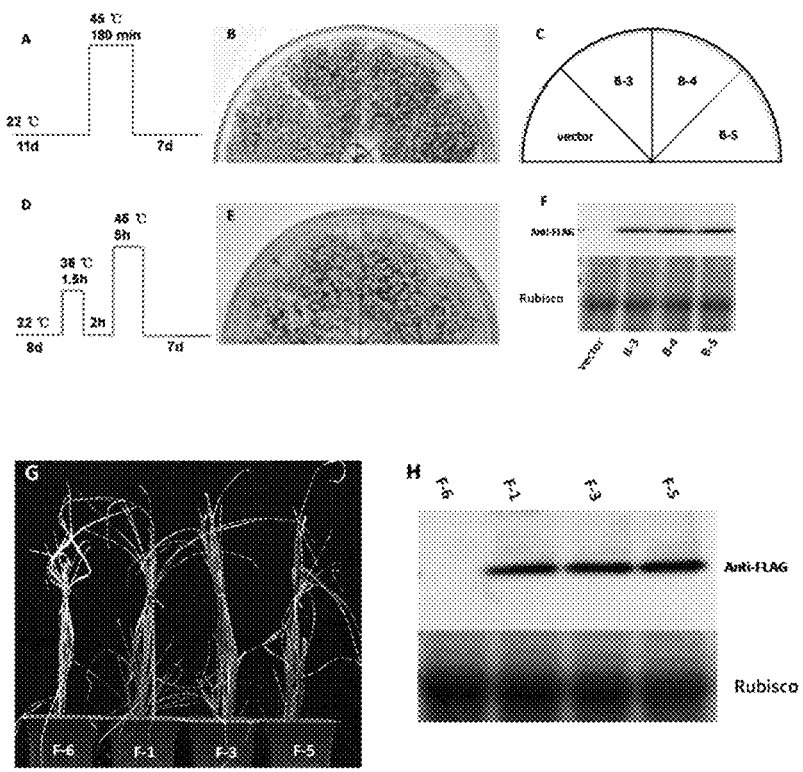

FIG. 5 shows that transgenic *Arabidopsis* and tall fescue with HTR1$^{CG14}$ overexpression demonstrates significantly enhanced high temperature resistance.

Wherein A-C show that basic high temperature resistance of transgenic *Arabidopsis* with HTR1$^{CG14}$ overexpression is significantly enhanced.

D-F show that overexpression of HTR1$^{CG14}$ can also significantly enhance the adaptive high temperature resistance of *Arabidopsis thaliana*. Wherein vector, transferred plasmid control; B-3, B-4, and B-5, positive transgenic lines with HTR1$^{CG14}$ overexpression.

G-H show that overexpression of HTR1$^{CG14}$ can significantly enhance the high temperature resistance of tall fescue. Wherein F-6, transgenic negative control; F-1, F-3 and F-5, positive transgenic lines with HTR1$^{CG14}$ overexpression.

(Note: A and D indicate two different high temperature treatments, detecting basic high temperature resistance and adaptive high temperature resistance of *Arabidopsis thaliana*, respectively; B and E show the phenotype of transgenic lines with HTR1$^{CG14}$ overexpression and controls thereof after high temperature treatment; C is the arrangement of the *Arabidopsis thaliana* lines in figures B and E; F is the detection results of exogenous HTR1$^{CG14}$ on protein level for *Arabidopsis thaliana* lines in figures B and E. G shows the phenotype of transgenic tall fescue lines with HTR1$^{CG14}$ overexpression and controls thereof after high temperature treatment; H is the detection results of exogenous HTR1$^{CG14}$ on protein level of the corresponding lines in G.)

Figure 6:
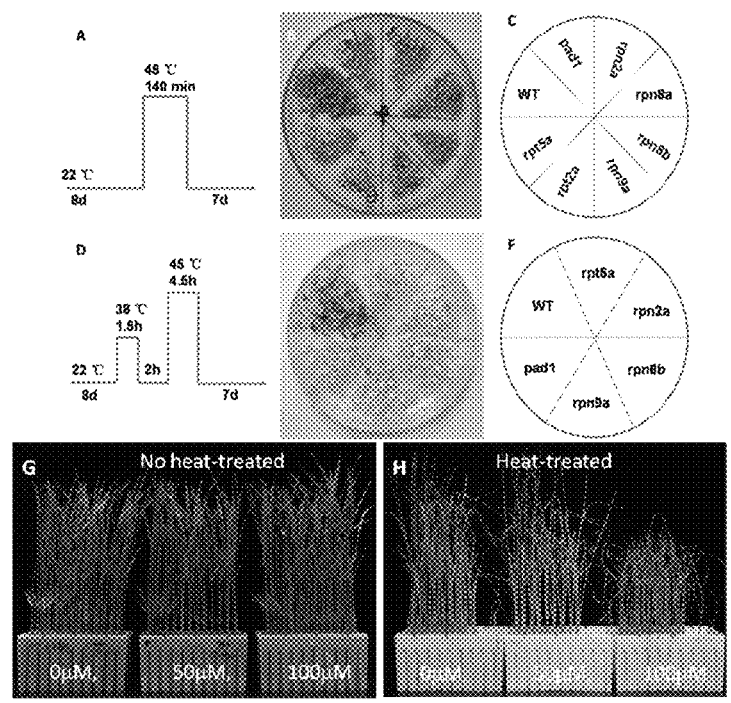

FIG. 6 shows that the degradation pathway of 26S proteasome participates in the plant high temperature response.

Wherein A-C show that the *Arabidopsis thaliana* mutants of 26S proteasome-associated subunits exhibit a lack of basic high temperature resistance.

D-F show that the adaptive high temperature resistance of the *Arabidopsis thaliana* mutants of 26S proteasome-associated subunits are also reduced.

G and H show that, under high temperature stress, blocking 26S proteasome degradation pathway with MG132 (from left to right, followed by 0 μM, 50 μM, 100 μM) can reduce the high temperature resistance of rice.

Figure 7A:
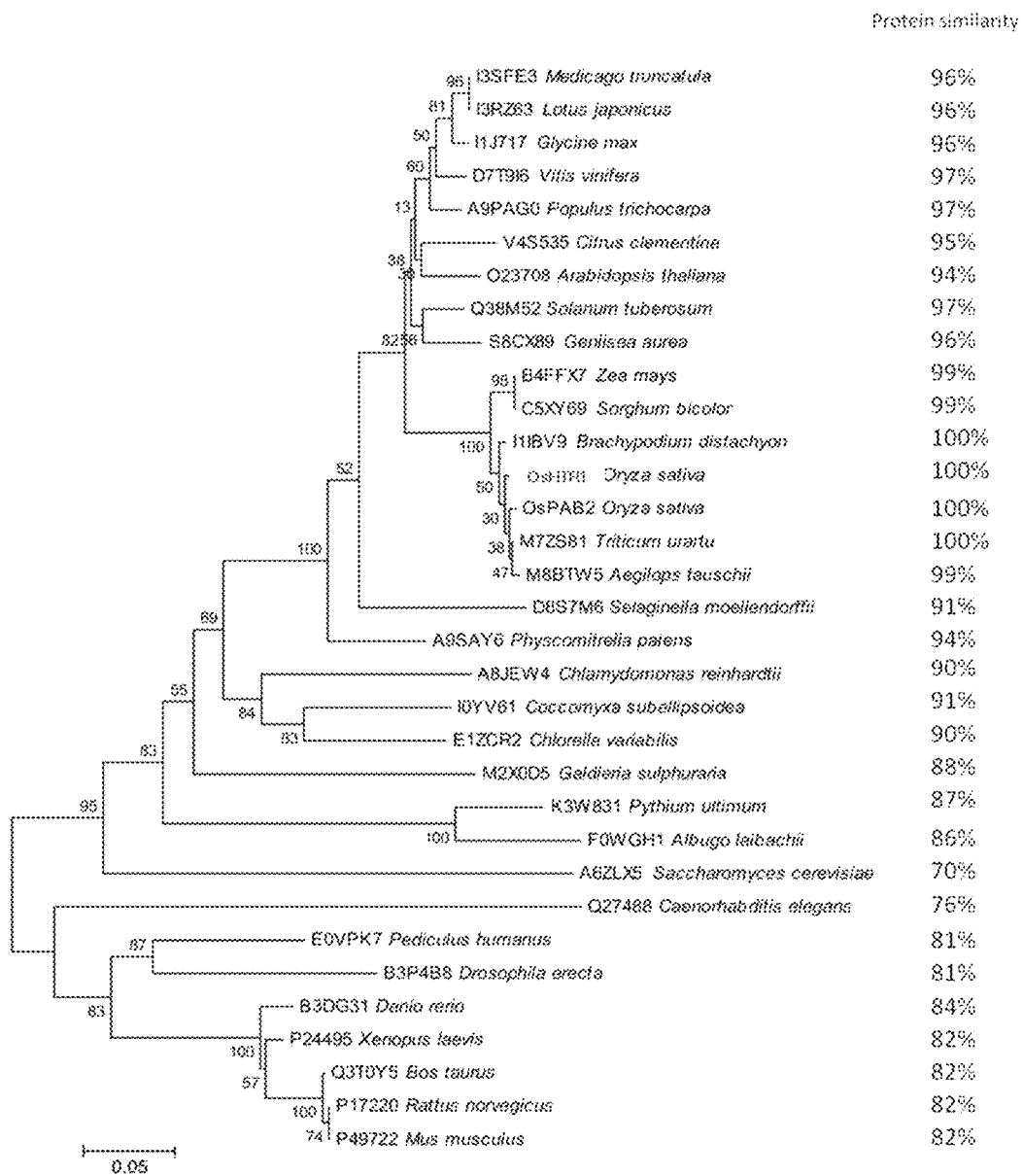
Figure 7B:
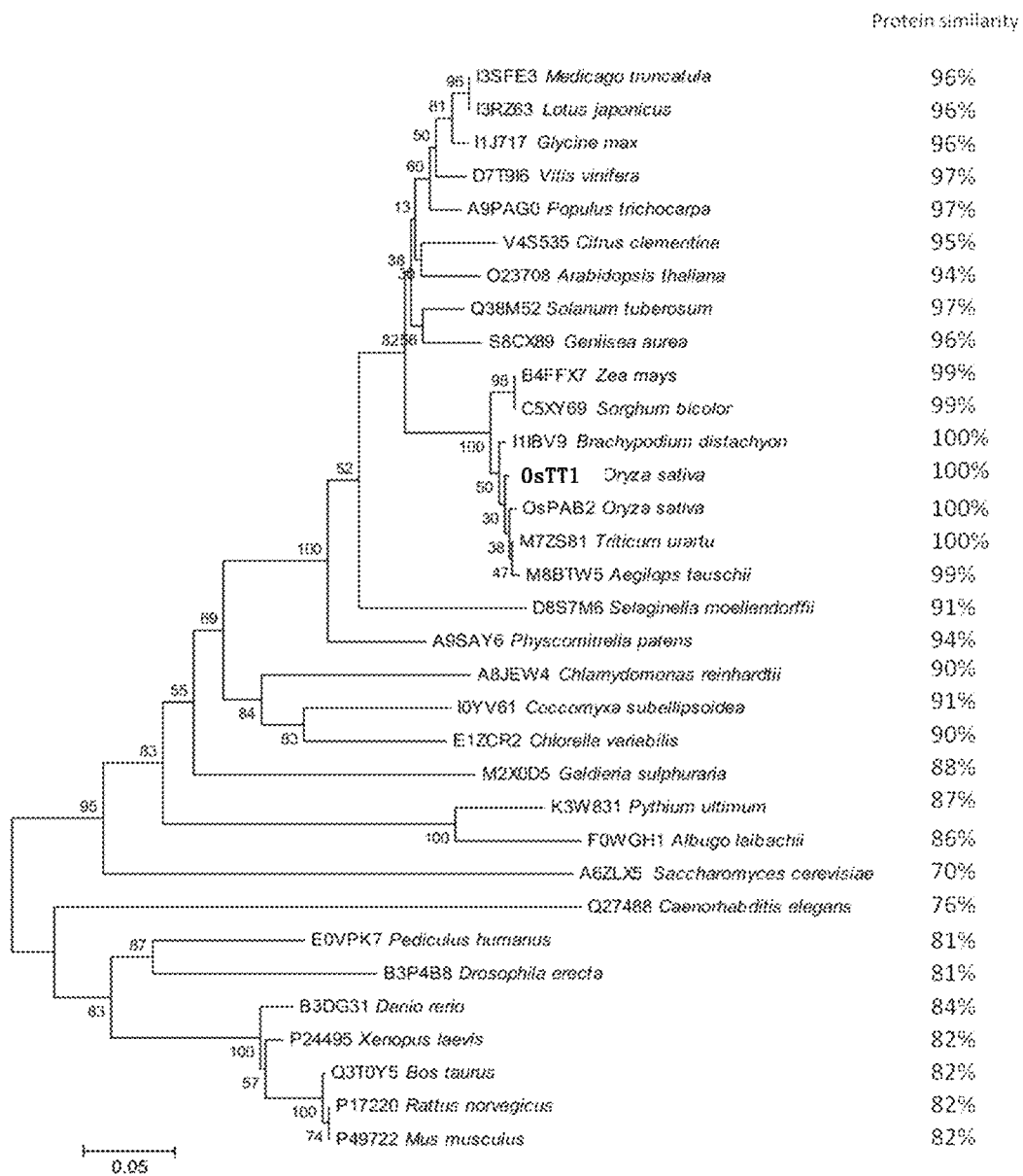

FIG. 7 shows that HTR1 gene is highly conserved in eukaryotes. The Latin text in FIG. 7A corresponds to the Chinese translation in FIG. 7B.

Figure 8:
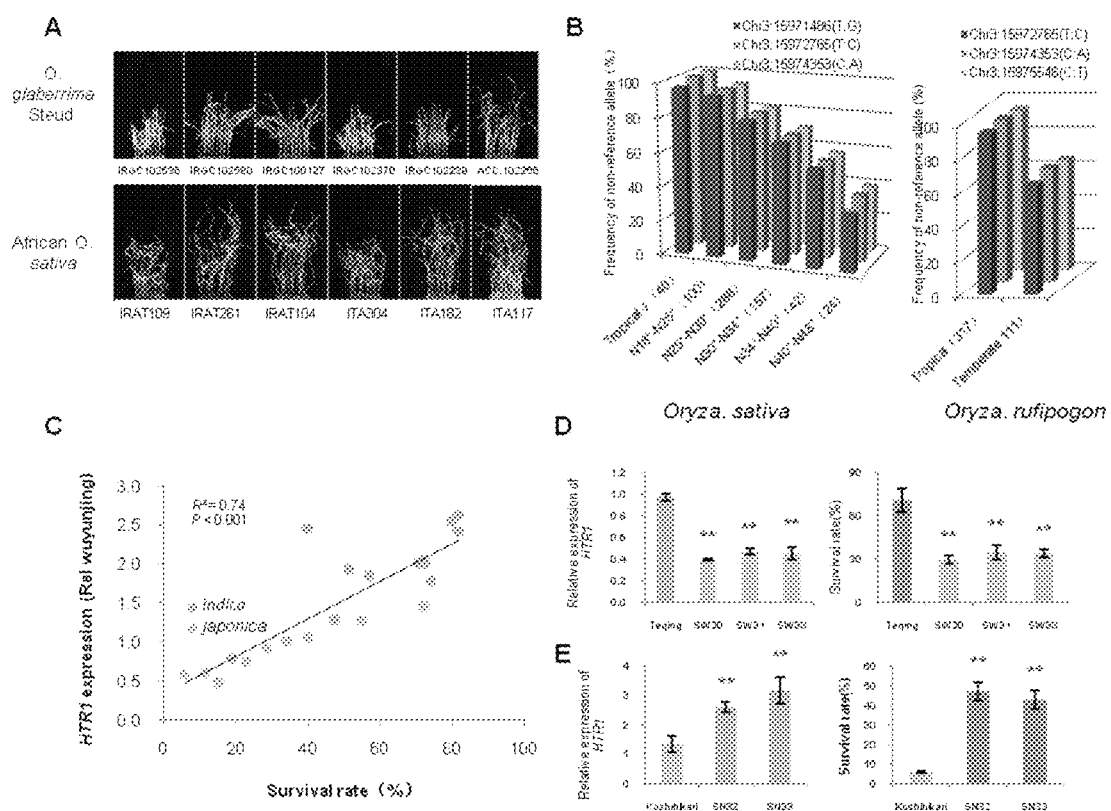

FIG. 8 shows distribution and functional differentiation of different haploid types of HTR1 gene.

Wherein A shows that the base mutation at position 296 (A to G) of HTR1 ORF region results in amino acid substitution (from WYJ$^{Arg}$ to CG14$^{His}$), thereby changing the protein functional activity of HTR1, which represents a specific strong heat resistant haploid type, and results in a stronger high temperature resistance of African rice.

B shows that the distribution of HTR1 in different haploid types in Asian rice is closely related to the temperature of the growth environment thereof (the lower latitude, the higher the climate temperature).

C-E show that the high temperature resistance of Asian rice is significantly related with the expression level of HTR1 gene.

DETAILED DESCRIPTION OF INVENTION

After extensive and intensive research, the inventor has successfully screened a new high temperature resistant protein (HTR1, High Temperature Resistance 1) from rice by map-based cloning technology for the first time and studied its function. It shows that the gene can enhance high temperature resistance of rice, therefore, there is an application prospect in the crop breeding for stress resistance. Based on the above findings, the present invention is completed.

In particular, the present inventors have used a chromosome segment substitution line (CSSL) and derived populations thereof constructed from African cultivated rice variety CG14 and *japonica* rice cultivar *Wuyun japonica* to precisely locate a main effect quantitative traits locus (QTL) for controlling high temperature resistance of rice: HTR1 (High Temperature Resistance 1). The results show that the encoding protein of the high temperature resistant gene of the present invention is the α2 subunit of 26S proteasome. Compared with the wild-type sequence, the high temperature resistant protein of the present invention has a change in one amino acid at the protein level, i.e., Arg at position 99 is mutated to His. Functional analysis shows that the mutation of this amino acid results in the activity for degraded and denatured protein of HTR1 in non-resistant high temperature rice (such as Wu yunjing) is lower than that of HTR1 of the present invention. The expression analysis results show that the high temperature resistance gene of the present invention is expressed in various tissues of rice, and the expression is obviously induced by high temperature. Genetic transformation experiments confirm that overexpression of HTR1 can significantly enhance high temperature tolerance of rice. After the transformation of HTR1 ino *Arabidopsis thaliana* and tall fescue, the positive lines demonstrate significantly enhanced high temperature tolerance, indicating that HTR1 can be applied to high-temperature resistant breeding of a large number of crops, including rice.

Definition

In th present invention, the term, such as "rice high temperature resistance protein 1", "HTR1 polypeptide", "high temperature polypeptide of the present invention", "the polypeptide of the present invention", "HTR1$^{CG14}$ protein" can be used interchangeably, all of which refer to a protein or polypeptide having an amino acid sequence (SEQ ID NO: 2) of high temperature resistant protein 1 in African rice, or a derived peptide or active fragment having the same high temperature resistant property.

As used herein, "isolation" refers to the material is isolated from its original environment (if it is a natural substance, the original environment is the natural environment). Such as, the polynucleotides and polypeptides in the native state of the living cells are not isolated and purified, but the same polynucleotides or polypeptides are isolated from other substances present in the natural state, then they are isolated and purified.

As used herein, "isolated rice high temperature resistance protein 1 or polypeptide" refers to rice high temperature resistance protein 1 is basically free of other proteins, lipids, carbohydrates or other substances that are naturally associated with it. The skilled in the art can purify rice high temperature resistance protein 1 using standard protein purification techniques. Substantially pure polypeptides can produce a single primary band on non-reductive polyacrylamide gels.

The Polypeptide(s) of the Present Invention

The polypeptide(s) of the present invention may be recombinant polypeptide(s), natural polypeptide(s), synthetic polypeptide(s), preferably recombinant polypeptide(s). The polypeptide(s) of the present invention may be naturally purified products, or chemically synthesized products, or produced from prokaryotic or eukaryotic hosts (e.g., bacteria, yeasts, higher plants, insects and mammalian cells) using recombinant techniques. The polypeptide(s) of the present invention may be glycosylated or may be non-glycosylated according to the host used in the recombinant production protocol. The polypeptide(s) of the invention may also include or may not include the starting methionine residue.

The present invention further includes the active fragments, derivatives and analogs of the rice high temperature resistance protein 1. As used herein, the terms "fragments", "derivatives" and "analogs" refer to the polypeptides basically maintaining the same biological function or activity of the natural rice high temperature resistance protein 1 of the present invention. The polypeptide fragments, derivatives or analogs of the present invention may be (i) a polypeptide with one or more conservative or non-conservative amino acid residues (preferably the conservative amino acid residues) being substituted, while such substituted amino acid residues may or may not be encoded by genetic code, or (ii) a polypeptide having substituted group(s) in one or more amino acid residues, or (iii) a polypeptide formed by fusion of the matured polypeptide with another compound (such as the compound that prolongs the half life of the polypeptide, such as polyethylene glycol), or (iv) a polypeptide formed with additional amino acid sequence fused to said polypeptide sequence (such as, leader sequence, secretion sequence, or a sequence or a protein sequence used to purify the polypeptide, or a fusion protein). According to the subject application, these fragments, derivatives and analogs are within the scope commonly known by the skilled person.

In the present invention, the term "rice high temperature resistance protein 1" refers to a polypeptide having a sequence of SEQ ID NO.:2 and the activity of rice high temperature resistance protein 1. The term further includes a variant form having a sequence of SEQ ID NO: 2 and the same function as rice high temperature resistance protein 1. These variant forms include, but are not limited to, deletions of one or more amino acids (typically 1-50, preferably 1-30, more preferably 1-20, most preferably 1-10), insert ions and/or substitutions, and the addition of one or several amino acids (typically at most 20, preferably at most 10, more preferably at most 5) at the C-terminus and/or N-terminus. For example, in the art, substitutions with close or similar amino acids do not normally alter the function of the protein. Also, for example, the addition of one or several amino acids at the C-terminus and/or the N-terminus will not normally alter the function of the protein. The term also includes active fragments and active derivatives of rice high temperature resistance protein 1.

The variant forms of the polypeptide include homologous sequences, conserved variants, allelic variants, natural mutants, induced mutants, protein encoded by a DNA capable of hybridizing to the DNA of rice high temperature resistance protein 1 under high or low stringency conditions, and a polypeptide or protein obtained using an antiserum against rice high temperature resistance protein 1. The present invention further provides other polypeptides, such as fusion proteins comprising rice high temperature resistance protein 1 or fragments thereof. In addition to the almost full length of the polypeptide, the present invention also includes a soluble fragment of rice high temperature resistance protein 1. Typically, the fragment has at least about 10 contiguous amino acids of the rice high temperature resistance protein 1, typically at least about 30 contiguous amino acids, preferably at least about 50 contiguous amino acids, more preferably at least about 80 contiguous amino acids, most preferably at least about 100 contiguous amino acids.

The invention also provides the analogues of the rice high temperature resistance protein 1 or the polypeptide. These analogues can differ from the naturally rice high temperature resistance protein 1 by amino acid sequence differences or by modifications that do not affect the sequence, or by both. These polypeptides include natural or induced genetic variants. Induced variants can be obtained by various techniques, such as random mutagenesis by irradiation or exposure to a mutagenic agent, but also by site-directed mutagenesis or other known molecular biology techniques. Also included are analogues which include residues other than those naturally occurring L-amino acids (e.g., D-amino acids) and non-naturally occurring or synthetic amino acids (e.g., β, γ-amino acids). It is to be understood that the polypeptides of the present invention is not limited to the representative polypeptides listed herein above.

Modification (usually do not change the primary structure) includes in vivo or in vitro chemical derivation of polypeptides, e.g., acetylation, or carboxylation. Also included is modification of glycosylation. Also included are sequences that have phosphorylated amino acid residues, e.g., phosphotyrosine, phosphoserine, phosphothreonine, as well as sequences that have been modified to improve their resistance to proteolytic degradation or to optimize solubility properties.

In the present invention, "the conservative variant polypeptide of the rice high temperature resistance protein 1" refers to a polypeptide formed by replacing at most 10, preferably at most 8, more preferably at most 5, most preferably 3 amino acids with the amino acid having similar or analogous property, compared with the amino acid sequence of SEQ ID NO.:2. These conservative variant polypeptides are preferably formed by carrying out the amino acid replacement according to Table 1.

Preferably, the polypeptide of the present invention (including a conservative variant polypeptide, or a derivative polypeptide) maintains the mutation from Arg to His at position 99 corresponding to SEQ ID NO.: 4.

TABLE 1

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |

TABLE 1-continued

| Initial residue | Representative substitution | Preferred substitution |
| --- | --- | --- |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Polynucleotides

The polynucleotide of the present invention can be in a form of DNA or RNA. DNA forms include cDNA, genomic DNA, or synthetic DNA. DNA can be single-stranded or double-stranded. DNA can be the coding strand or the non-coding strand. The coding region sequence encoding mature polypeptide can be identical to the coding region sequence of SEQ ID NO.: 1 or can be a degenerate variant thereof. As used herein, "a degenerate variant" in the present invention refers to a nucleic acid sequence encoding a protein having SEQ ID NO: 2 but different from the coding region sequence shown in SEQ ID NO: 1.

The polynucleotide encoding the mature polypeptide of SEQ ID NO: 2 comprises a coding sequence encoding only the mature polypeptide; a coding sequence of the mature polypeptide and various additional coding sequences; a coding sequence (and optionally additional coding sequence) of the mature polypeptide, and non-coding sequence.

The term "a polynucleotide encoding a polypeptid" may be a polynucleotide that encodes the polypeptide, or a polynucleotide that also includes additional coding and/or non-coding sequences.

The present invention also relates to variants of the polynucleotides as described above, which encode fragments, analogs and derivatives of polypeptides or polypeptides having the same amino acid sequence as the present invention. Variants of such polynucleotides may be naturally occurring allelic variants or non-naturally occurring variants. Such nucleotide variants include substitutions of variants, deletions of variants, and insertions of variants. As is known in the art, an allelic variant is an alternative form of a polynucleotide, which may be a substitution, deletion or insertion of one or more nucleotides, but the function of the polypeptide encoded by the polynucleotide will not be substantially altered.

The present invention also relates to polynucleotides that hybridize to the sequences as described above and having at least 50%, preferably at least 70%, more preferably at least 80% identical between the two sequences. In particular, the present invention relates to polynucleotides that can hybridize to the polynucleotides of the present invention under stringent conditions. In the present invention, "stringent conditions" mean: (1) hybridization and elution at lower ionic strength and higher temperature, such as 0.2×SSC, 0.1% SDS, 60° C.; or (2) hybridization adding a denaturant, such as 50% (v/v) formamide, 0.1% calf serum/0.1% Ficoll, 42° C., or the like; or (3) hybridization only occurs when the identity between the two sequences is at least 90%, more preferably 95% or more. And the polypeptide encoded by the hybridizable polynucleotide has the same biological function and activity as the mature polypeptide shown in SEQ ID NO: 2.

The present invention also relates to a nucleic acid fragment that hybridizes to the above sequences. As used herein, "a nucleic acid fragment" is at least 15 nucleotides in length, preferably at least 30 nucleotides, more preferably at least 50 nucleotides, and most preferably at least 100 nucleotides. Nucleic acid fragments can be used for nucleic acid amplification techniques (such as PCR) to determine and/or isolate polynucleotides encoding rice high temperature resistance protein 1.

Promoters Specifically Responsive to High Temperature

The present invention also provides a sequence for a promoter (specifically responsive to high temperature) that specifically drives HTR1 at high temperature and a use thereof in the high temperature resistance breeding of variety crops. A representative promoter sequence is shown in SEQ ID NO.: 27 and 28. It is to be understood that the term "a promoter specifically responsive to high temperature of the present invention" also includes not only the full length promoter sequences as shown in SEQ ID NO.: 27 and 28, but also an active fragment or a core fragment (including a promoter fragment containing a nucleotide variant) derived from the sequence (SEQ ID NO.: 27 or 28) and having the same or equivalent specific response to high temperature function.

Using the promoter specifically responsive to high temperature, the transgenic plants (such as wheat, maize, sorghum and other food crops, vegetable, fruits, flowers and plants, and pasture), which can specifically induce the expression of exogenous gene in response to high temperature, can be prepared.

In addition, based on the promoter of the present invention specifically responsive to high temperature, a DNA base sequence of a homologous gene promoter in other plants (including other crops) can also be obtained.

Recombinant Technology and Plant Improvement

A nucleotide full length sequence or fragment thereof of the rice high temperature resistance protein 1 of the present invention can generally be obtained by a PCR amplification method, a recombinant method or an artificial synthetic method. For a PCR amplification method, primers can be designed according to the relevant nucleotide sequences disclosed in the present invention, particularly the open reading frame sequences, and the commercially available cDNA libraries or cDNA libraries prepared by the conventional methods known to the skilled in the art were used as a template, and amplified and the relevant sequences were obtained. When the sequence is longer, two or more PCR amplifications are usually needed, and then each of the amplified fragments are spliced together in the correct order.

Once the relevant sequence is obtained, the relevant sequence can be obtained in bulk using a recombination method. Usually cloned into a vector, then transferred into a cell, and then the relevant sequence is separated and obtained from the proliferation of host cells by the conventional method.

In addition, the relevant sequence can also be synthesized using artificial synthesis methods, particularly when the fragment is shorter. In general, a very long fragment can be obtained by firstly synthesizing multiple small fragments and then ligating them.

At present, a DNA sequence encoding the protein of the present invention (or fragments thereof, or derivatives thereof) can completely be obtained by chemical synthesis. The DNA sequence can then be introduced into a variety of existing DNA molecules (or vectors) and cells known in the art. In addition, mutations can also be introduced into the protein sequences of the present invention by chemical synthesis.

The present invention also relates to a vector containing a polynucleotide of the present invention, and a host cell produced by genetic engineering using a vector or a rice high temperature resistance protein 1 encoding sequence of the present invention, and a method for producing the polypeptide of the present invention by recombinant techniques.

With the conventional recombinant DNA technique (Science, 1984; 224: 1431), the polynucleotide of the present invention can be used to express or produce the recombinant rice high temperature resistance protein 1. Generally, the method comprises the following steps:

(1) Transforming or transfecting a suitable host cell with a polynucleotide or variant thereof encoding the rice high temperature resistance protein 1 of the present invention or a recombinant expression vector containing said polynucleotide;

(2) Culturing the host cell in a suitable culture medium;

(3) Isolating and purifying protein from the culture medium or cell.

In the present invention, the polynucleotide sequence of the rice high temperature resistance protein 1 can be inserted into a recombinant expression vector. The term "a recombinant expression vector" refers to bacterial plasmids, phages, yeast plasmids, plant cell viruses, mammalian cell viruses or other vectors well known in the art. In a word, any plasmid and vector can be used as long as it can be replicated and stabilized in the host. An important feature of an expression vector is that it usually contains a replication origin, a promoter, a marker gene, and a translation control element.

An expression vector containing an encoding DNA sequence of a rice high temperature resistance protein 1 and a suitable transcription/translation control signal can be constructed by the methods well known to the skilled in the art. These methods include recombinant DNA technology in vitro, DNA synthesis technology, recombination techniques in vivo. The DNA sequence described herein can be operably linked to a suitable promoter in an expression vector to direct mRNA synthesis. The expression vector also includes a ribosome binding site for translation initiation and a transcription terminator.

In addition, the expression vector preferably comprises one or more selectable marker genes to provide the selection of phenotypic traits for the transformed host cells, such as dihydrofolate reductase for eukaryotic cell culture, neomycin resistance, and green fluorescent protein (GFP), or tetracycline or ampicillin resistance for *E. coli*.

A vector comprising an appropriate DNA sequence and a suitable promoter or a control sequence as described above can be used to transform an appropriate host cell to enable it to express the protein.

A host cell can be a prokaryotic cell, such as a bacterial cell; or a lower eukaryotic cell, such as a yeast cell; or a higher eukaryotic cell, such as a plant cell (such as a cell of crop and forestry plant). Representative examples are: *Escherichia coli, Streptomyces, Agrobacterium*; a fungal cell such as yeast; a plant cell and the like.

When the polynucleotides of the present invention are expressed in a higher eukaryotic cell, the transcription will be enhanced if an enhancer sequence is inserted into a vector. The enhancer is a cis-acting factor of DNA, usually about 10 to 300 base pairs, acting on the promoter to enhance the transcription of the gene.

How to select an appropriate vector, promoter, enhancer and host cell will be clearly known by the skilled in the art.

Transformation of host cells with recombinant DNA can be carried out using conventional techniques well known to the skilled in the art. When the host is a prokaryote such as E. coli, competent cells capable of absorbing DNA can be harvested after the exponential growth phase and treated with $CaCl_2$, the steps used are well known in the art. Another method is to use $MgCl_2$. If necessary, the transformation can also be carried out by means of electroporation. When the host is an eukaryote, the following DNA transfection methods are available: calcium phosphate coprecipitation, conventional mechanical methods such as microinjection, electroporation, liposome packaging, and the like.

Agrobacterium or gene gun transformation method, such as leaf discs, can be used to transform a plant. For the transformed plant cell, tissue or organ, the conventional method can be used to regenerate a plant, thereby obtaining plants resistant to high temperature changes.

The obtained transformants can be cultured by a conventional method to express a polypeptide encoded by a gene of the present invention. According to the host cell used, the medium used in the culture may be selected from a variety of conventional media. And the host cell can be cultured under conditions suitable for the growth of the host cell. After the host cell grows to the appropriate cell density, the selected promoter is induced with a suitable method, such as temperature conversion or chemical induction, and the cells are incubated for a further period of time.

The recombinant polypeptide in the method above may be included in the cells, or expressed on the cell membrane, or secreted out of the cell. If desired, the physical, chemical and other properties can be utilized in various isolation methods to isolate and purify the recombinant protein. These methods are well-known to those skilled in the art. The examples of these methods include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

The recombinant rice high temperature resistance protein 1 has uses in many aspects. For example, it can be used in screening compounds, polypeptides or other ligands that promote or antagonize the function of rice high temperature resistance protein 1. The expressed recombinant rice high temperature resistance protein 1 can be used in screening valuable polypeptide molecules that can stimulate the function of rice high temperature resistance protein 1 in a polypeptide library.

In another aspect, the present invention also includes polyclonal and monoclonal antibodies, in particular monoclonal antibodies specific for polypeptides encoded by DNA of rice high temperature resistance protein 1 or a fragment thereof. The present invention includes not only intact monoclonal or polyclonal antibodies, but also antibody fragments with immunological activity, or chimeric antibodies.

The antibodies of the present invention may be prepared by various techniques known to the skilled in the art. For example, a purified rice high temperature resistant protein 1 gene product or an antigenic fragment thereof can be administered to an animal to induce the production of a polyclonal antibody. Various antibodies of the present invention can be obtained by conventional immunization techniques using fragments or functional regions of the rice high temperature resistance protein 1 gene product. These fragments or functional regions can be prepared using recombinant methods or synthesized using peptide synthesizers. An antibody that binds to an unmodified form of a rice high temperature resistance protein 1 gene product can be produced by immunizing an animal with a gene product produced in a prokaryotic cell (e.g., E. coli); an antibody that binds to a post-translational modified form (such as a glycosylated or phosphorylated protein or polypeptide) can be obtained by immunizing an animal with a gene product produced in eukaryotic cells (e.g., a yeast or insect cell). Anti-rice high temperature resistance protein 1 antibodies can be used to detect the rice high temperature resistance protein 1 in a sample.

The present invention also relates to a method for the quantitative and targeted detection of the rice high temperature resistance protein 1 levels. These tests are well-known in the art. The level of rice high temperature resistance protein 1 tested in the experiment can be used to explain the high temperature resistance of rice high temperature resistance protein 1.

A method for detecting the presence of rice high temperature resistance protein 1 in a sample is to detect using a specific antibody against rice high temperature resistance protein 1, comprising: contacting the sample with the specific antibody against rice high temperature resistance protein 1; and observing the formation of an antibody complex; the formation of the antibody complex indicates that the presence of rice high temperature resistance protein 1 in the sample.

A portion or all of the polynucleotides of the present invention may be immobilized on a microarray or DNA chip (also referred to as a "gene chip") as a probe for the analysis of differential expression analysis of genes in a tissue. The specific primers of rice high temperature resistance protein 1 are used for In vitro amplification of RNA-polymerase chain reaction (RT-PCR), which can also detect the transcription product of rice high temperature resistance protein 1.

In an example of the present invention, an isolated polynucleotide is provided, which encodes a polypeptide having the amino acid sequence of SEQ ID NO: 2. The polynucleotide of the present invention is isolated from rice and the sequence thereof is shown in SEQ ID NO: 1, which contains a polynucleotide sequence of 708 bases in full length, the open reading frame thereof is at positions 1-705, and encodes a full length of 235 amino acids of rice high temperature resistance protein 1 (SEQ ID NO: 2).

In addition, molecular markers H1, H6 and H9 (SEQ ID NO.a-f) derived from a HTR1 gene and SNPs at positions 222 (C to T) and 296 (A to G) of the HTR1 ORF region, and 3 molecular markers used to identify HTR1 haplotypes of SNP in FIG. 8B are provided by the present invention, and these molecular markers can be used to assist in the selection of new varieties of heat resistant (high temperature resistant) rice.

The major advantages of the present invention include:

(a) Rice high temperature resistance protein 1 has a function of significantly improving resistance of a plant to high temperature, which provides a new way to change the high temperature resistance of the plant, thereby having a great application prospect.

(B) By introducing a HTR1 gene, the high temperature resistance of the existing excellent crop varieties can be changed, thereby obtaining high-temperature resistant wheat, rice and other crops or other varieties such as forest grass, fruit trees, flowers and so on, solving the practical problems existed in the agricultural and forestry production.

(c) The high temperature resistant protein of the present invention plays an important role in adapting the changes of the ambient temperature to the rice and has an important practical significance for the introduction of different regions.

The invention will be further illustrated with reference to the following specific examples. It is to be understood that these examples are only intended to illustrate the invention, but not to limit the scope of the invention. For the experimental methods in the following examples without particular conditions, they are performed under routine conditions (eg. Sambrook et al., Molecular Cloning: A Laboratory Manual (New York: Cold Spring Harbor Laboratory Press, 1989) or as instructed by the manufacturer. Unless otherwise specified, all percentages, ratios, proportions or parts are by weight.

Materials

CG14 was obtained from the international rice germplasm.

Wu yunjing was available from the National Rice Germplasm Resource Library of China.

Example 1

Material Culture and Treatment

The number of seeds to be identified in the rice lines was counted. Before soaking, the seeds were firstly placed in an oven at 42° C. for 2 weeks to break the dormancy. Then, the seeds were soaked in water at room temperature for 2 days, and the water was changed every day to avoid seed rotten. The seeds were placed in a 37° C. incubator for germination on the third day. After 3 days, each batch of 16 germinated seeds was sown in a 96-well plate where the bottom of the tube have been cut off, tap water was filled, and the plate was covered with plastic wrap, and cultured in a light incubator at 30° C. After 1 day, the culture conditions were adjusted to 28° C. during the day, 13 hours, 24° C. during the night for 11 hours. The plate was placed in the light incubator for 2 days, then the plastic wrap was removed, and the water was changed to ½×rice culture medium with 1× at the fourth day. Afterwards, the culture medium was changed once every other day. When the rice seedlings were grown to 2 leaves-1 heart (ie, the first and second leaves had been fully developed, the third piece of new leaves just emerged, about 12 days), high temperature treatment was performed. During the treatment, it was set as daytime 45° C. for 13 hours and night 45° C. for 11 hours. After co-treated for a certain time, fresh nutrient solution was added, placed in the normal conditions to resume the growth for about a week. The survival situation of each line was observed and recorded.

High temperature treatments for the rice (NIL (CG14) and NIL (WYJ), transgenic lines and their control) during flowering and filling stages were carried out in microclimate chambers. The rice plants grown to the booting stage or the flowering stage in the field were transplanted into the climate chamber, adapted for 3-5 days under the culture condition of 28° C., and then subjected to high temperature treatment at 38° C. during the day and 35° C. during night, wherein treated for 5 days during the flowering period, treated for 12 days during the filling period. After the treatment, the culture conditions were restored to 28° C. until the seeds were mature and the final yield traits were investigated.

Figure 2:
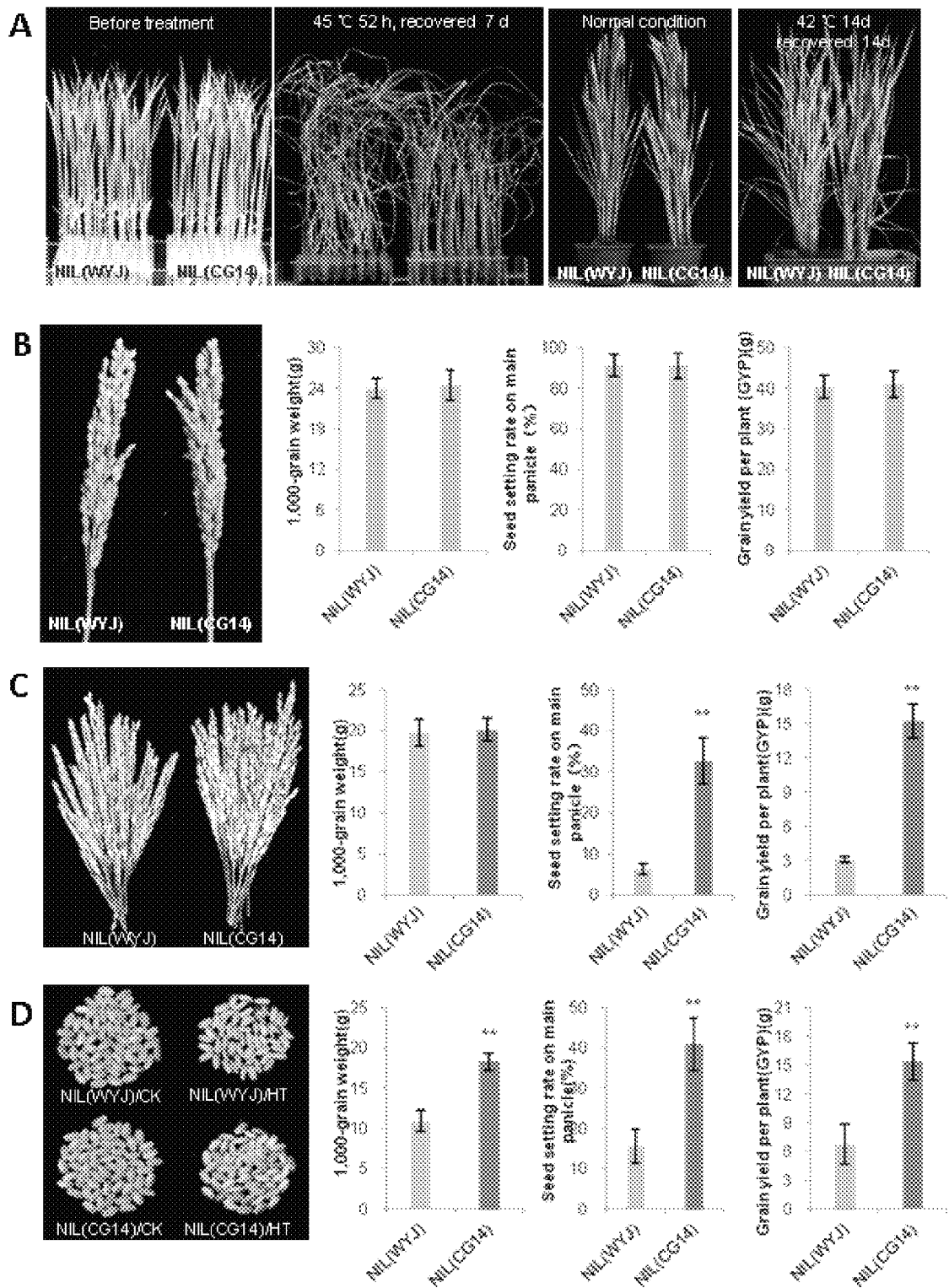
FIG. 2 shows that, compared with control (NIL (WYJ)) (carrying HTR1$^{WYJ}$ gene locus from Asian rice), NIL (CG14) with the African rice high temperature resistant gene HTR1$^{CG14}$ demonstrates a significantly enhanced high temperature resistance.

The results show that NIL (CG14) carrying African rice $HTR1^{CG14}$ gene locus demonstrates a significantly obvious high temperature resistance compared with the control (NIR (WYJ) (carrying the Asian rice $HTR1^{WYJ}$ gene locus) at seedling stage or at mature stage (flowering stage and grain filling stage) (FIG. 2); $HTR1^{CG14}$ transgenic rice lines also have a greater heat resistance (high temperature resistance) at all times (FIG. 4).

*Arabidopsis thaliana* plants were grown on MS plate culture medium, alternating day and night at 16/8-h (22° C./18° C.). The seedlings grown for 11 days were subjected to high temperature treatment (using different treatments for basic high temperature resistance and adaptive high temperature resistance, FIG. 5, FIG. 6), and then resumed for about 1 week to investigate the phenotype.

It is found that transgenic plants with $HTR1^{CG14}$ overexpression are significantly more resistant to high temperature (FIG. 5), whereas mutants of other subunits in the 26S proteasome other than the α2 subunit show high temperature sensitive phenotypes (FIG. 6), i.e., after the mutation of other subunits in the 26S protease, the high temperature resistance of plants is significantly reduced.

*Festuca arundinacea* was planted in artificial soil with conditions of 16/8-h (18° C.) alternating day and night. The transgenic plants with the same growth status and their corresponding control were selected for high temperature treatment, treated at 42° C. for 48 hours and resumed for two weeks. It is observed that the transgenic plants with $HTR1^{CG14}$ overexpression had significantly enhanced heat resistance than the control (FIG. 5).

Example 2

The Discovery, Localization Cloning of HTR1 and NIL Breeding

In this example, CG-14 was used as a donor parent, Wu yun *Japonica* was used as a recurrent parent, and a set of chromosome segment substitution lines (CSSLs) were constructed and used for high temperature screening.

After repeated testing and repeated validation, a stable line showing high temperature tolerance was repeatedly identified, which showed a significantly stronger high temperature tolerance than the recurrent parent after the treatment at 45° C. for 52 hours In order to genetically locate the target gene, the substitution line was backcrossed with *Wuyun japonica*, and then subjected to selfing, thereby obtaining $F_2$ population. Linkage analysis and initial location were performed with the isolated $F_2$ population. Fine mapping and breeding of NIL (near-isogenic line) were performed with an expanded $F_2$ population and a further backcross population. Genomic sequences of some African rice were sequenced by segmented cloning through reference to the sequence information of the target region PAC clone, and some molecular markers with obvious polymorphism between two parents were developed. Wherein the following three molecular markers were used for the final fine mapping and molecular marker-assisted selection of NIL:

5' oligonucleotide primer sequence of Marker-H1 is:

```
                                        (SEQ ID NO: 5)
        5'- TGGGTTTTGAGGACTTCC -3';
```

3' primer sequence is:

(SEQ ID NO: 6)
5'- CATTGGGACATATGTAGC -3'.

5' oligonucleotide primer sequence of Marker-H6 is:

(SEQ ID NO: 7)
5'- CTGGATACACAGTTGTCC -3';

3' primer sequence is:

(SEQ ID NO: 8)
5'- AATCGATCGATTGTCCCG -3'.

5' oligonucleotide primer sequence of Marker-H9:

(SEQ ID NO: 9)
5'- CGACGACAAGTACGATCG -3';

3' primer sequence is:

(SEQ ID NO.: 10)
5'- TGATCTCTCGATCCACAC -3'.

More than 6,000 $F_2$ individuals were screened by using these molecular markers, and a total of nearly 1,000 individuals were obtained with exchange in the substitution section. A part of individuals with key exchange were selfed to produce homozygotes with a variety of genotypes. The homozygotes were repeatedly identified for high temperature tolerance. Finally, the seeds of the key plants with exchange at the target location ($BC_4F_3$), and A, B control for $BC_4F_3$ with the same background were subjected to phenotypic identification.

Combined with these phenotypic identification results, high precision linkage analysis was performed for the target QTL. Finally, HTR1 was located in the region of 12.69 kb, which contained two candidate genes.

Based on a further experimental result, a candidate gene for encoding the α2 subunit of 26S proteasome is identified as HTR1 gene.

Figure 1:
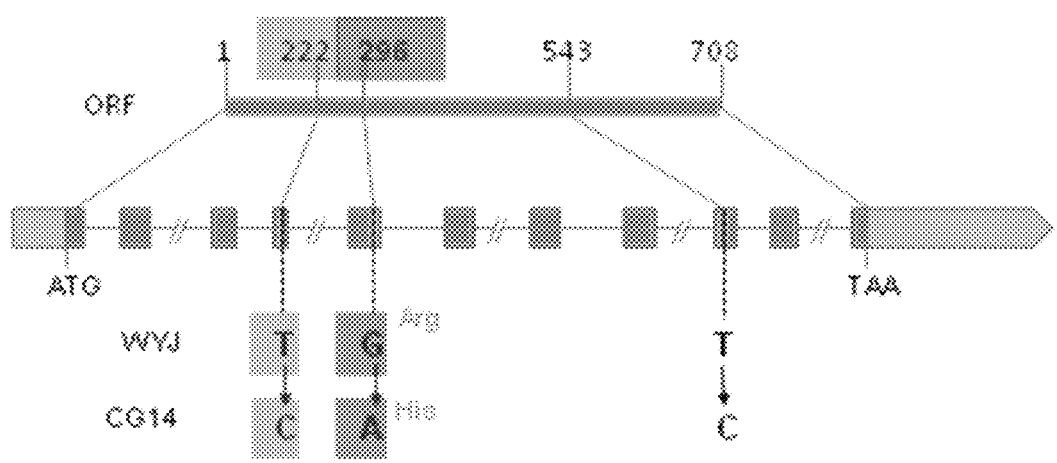
FIG. 1 shows the structure of HTR1 gene in rice. Nucleotide mutation at 296 position (A to G) results in amino acid substitution (from WYJ$^{Arg}$ to CG14$^{His}$), thereby changing the protein functional activity of HTR1 and representing a strong heat resistant haplotype. SNP at position 222 (C to T) does not result in the change of the encoded protein sequence, however, the SNP represents a haplotype of HTR1. That is, the SNP can be used to identify haplotype of HTR1 in different rice cultivars.

According to the information and relevant literatures of the rice gene annotation database of RAP-DB and MSU, the rice genomic sequence and cDNA sequence of HTR1 candidate gene were cloned and the sequences of the two parents were compared by the inventors (FIG. 1).

The results show that there are 3 base mutations in ORF region between the HTR1$^{CG14}$ in the high temperature resistant African cultivated rice CG14 and the allele HTR1$^{WYJ}$ in the Wuyun japonica, wherein 2 of which are synonymous mutations (positions 222 and 543), while the base mutation at position 296 (A to G) results in amino acid substitution (from WYJ$^{Arg}$ to CG14$^{His}$), thereby affecting the protein functional activity of HTR1, and making the rice have different high temperature resistance.

The cDNA sequence of HTR1 gene is shown in SEQ ID NO.:1, encoding a protein of 235 amino acids in length (SEQ ID NO.: 2). HTR1 genome has 6292 bp in full length (SEQ ID NO: 29), containing 11 exons.

In addition, the corresponding genomic sequence of CG14 is shown in SEQ ID NO.: 29, wherein positions 1-1909 is the promoter sequence and positions 1910-1912 is the initiation codon of ATG, with 11 exons in total, which is positions 1910-1947, 2038-2117, 3252-3318, 3405-3446, 4105-4184, 4346-4411, 4705-4773, 4935-5022, 5244-5305, 5385-5452, and 5855-5902, respectively. Wherein a base substitution (4173: G to A) is occurred on the fifth exon, making the amino acid corresponding to position 99 of the amino acid sequence of Asian cultivated rice (SEQ ID NO.: 4) mutated from Arg to His in African rice CG14 (the specific sequence is shown in SEQ ID NO.: 2), i.e., Arg99→His99 (His codon in CG14 corresponds to positions 4172-4174 of CAT).

Correspondingly, the corresponding genomic sequence of Asian cultivated rice (WJY) is shown in SEQ ID NO.: 30.

Example 3

Transgenic Experiment of HTR1 Rice

In this example, the rice transformation experiment was carried out using the rice immature embryo transformation method mediated by *Agrobacterium tumefaciens* EHA105. Details as follows:

3.1 Construction of Transgenic Plasmid for HTR1 Gene Overexpression:

A pHB vector was used for the overexpression of HTR1, which is from a plant expression vector pCAMBIA3301 (available from CAMBIA, Canberra, Australia) and contains a bacteria replication origin (ori), a kanamycin resistance gene (Kanr), a hygromycin resistance gene (Hygr), a herbicide resistance gene (Bar), two CaMV35S promoters in series, a termination signal sequence of a NOS gene, and the restriction endonuclease cloning site (MCS) between the latter two. After cloning the encoding sequence of the target gene into CaMV35S promoter, high expression can be obtained under its strong drive.

For cloning HTR1 encoding sequence, CG14 and *Wuyun japonica* RNA were used as a template to synthesize the first strand of cDNA, and the PCR oligonucleotides at 5' and 3' ends of the DNA sequence were used as primers (SEQ ID NOs: 11 and 12), and amplified with high fidelity Taq enzyme of Kod to obtain a cDNA amplification product of 1,023 bp containing a full length ORF. The product was added with polyA and cloned into pTA2 vector (purchased from TOYOBO), and a number of recombinants were sequenced to verify the sequence. The recombinant transitional plasmid vector was referred to as HTR1-CG14-PTA2 and HTR1-WYJ-PTA2.

5' oligonucleotide primer sequence is:

(SEQ ID NO: 11)
5'-AAGCAATCGTAGTTAGCAGA -3';

3' primer sequence is:

(SEQ ID NO.: 12)
5'-TTTGGCAAGAAGTAAAACAG-3'.

The full length ORF of HTR1 was cloned by using the transitional vector as template and the PCR oligonucleotides containing 5' and 3' ends of the cleavage site as primers (SEQ ID NO.: 13 and 14), the PCR product and the pHB vector were digested with SacI and XbaI and then a viscous terminal was ligated, the conjugate was transformed into *Escherichia coli* strain DH5α and the transformants were screened on LB medium containing Kan (50 μg/ml), the single colony was selected and the plasmid was extracted, a clone with about 780 bp fragment was selected by digestion with SacI and XbaI, and the nucleotide sequence is verified by M13 universal primer sequencing, thereby successfully constructing plasmid HTR1$^{CG14}$-pHB and HTR1$^{WYJ}$-pHB.

5' oligonucleotide primer sequence is:

(SEQ ID NO.: 13)
5'-CGAGCTCATGGGCGACAGCCAGTACTCCTTCTCCC-3';

3' primer sequence is:

(SEQ ID NO.: 14)
5'-GCTCTAGACTATTATTTGTCATCGTCATCTTTGTAGTCCGCTGAGCC

TCCTCCTTCCACCTCTTCCAAGAAATCCTTG-3'.

Wherein in the sequence of SEQ ID NO.: 14, a FLAG tag was added after the protein sequence of HTR1.

3.2. Construction of HTR1-Knockdown Expression Plasmid:

The knockdown of HTR1 is achieved by means of artificial microRNAs. The genomic DNA of rice was firstly amplified with three pairs of 5' and 3' end PCR oligonucleotide primers (SEQ ID NO.: 15 and 16; 17 and 18; 19 and 20) to obtain three products 111 bp, 87 bp and 112 bp in length, respectively, and then nested PCR was performed by using SEQ ID NO.: 15 and 20 as primer and a mixture of the above three PCR products as a template, and to obtain a fragment of 262 bp. The fragment and p1301SN vector were double digested with BamHI and KpnI, and then the viscous terminal was ligated. The conjugate was transformed into *Escherichia coli* strain DH5α and the transformants were screened on LB medium containing Kan (50 µg/ml), the single colony was selected and the plasmid was extracted, a clone with about 262 bp fragment was selected by digestion with SacI and XbaI, and the nucleotide sequence is verified by sequencing, thereby successfully constructing HTR1$^{CG14}$-knockdown plasmid.

The primers used for the construction are:

(SEQ ID NO.: 15)
5'-CGGGGTACCCAGCAGCAGCCACAGCAAA-3';

(SEQ ID NO.: 16)
5'-AGTGAGACAAATTATTCCACCTGCAGGAGATTCAGTTTGA-3'.

(SEQ ID NO.: 17)
5'-TGCAGGTGGAATAATTTGTCTCACTGCTGCTGCTACAGCC-3';

(SEQ ID NO.: 18)
5'-CTCAGGTCGAAAAATTTGTCTCATTCCTGCTGCTAGGCTG-3'.

(SEQ ID NO.: 19)
5'-AATGAGACAAATTTTTCGACCTGAGAGAGGCAAAAGTGAA-3';

(SEQ ID NO.: 20)
5'-CGCGGATCCGCTGCTGATGCTGATGCCAT-3'.

3.3. EHA105-Mediated Transformation in Rice:

The recombinant plasmid constructed as above was introduced into conventional *Agrobacterium* strain EHA105 by freeze-thaw method. 0.5-1 µg (about 10 µl) of plasmid DNA was added into each 200 µl of EHA105 competent cell and then mixed well, placed on the ice, in the liquid nitrogen and 37° C. water bath for 5 minutes, successively; diluted to 1 ml with the fresh YEB liquid medium, cultured by shaking for 2-4 hours at 28° C.; and 200 µl was applied to YEB plates containing antibiotic Kan (50 µg/ml) and cultured at 28° C. for 2-3 days. The grown colonies were inoculated by streaking on a YEB plate containing antibiotics for selecting single colonies, and the above steps were repeated for 3 times. Referring to the method of Hiei et al. (1994), a single colony of *Agrobacterium tumefaciens* was selected from YEB plated, inoculated into 3 ml of antibiotic-containing YEB liquid medium, and incubated overnight at 28° C. On the next day, the culture was transferred to a 50 ml of antibiotic-containing AB liquid medium at 1% inoculation amount, and cultured by shaking at 200 rpm until OD600 was about 0.6 to 0.8. The fresh *Agrobacterium* bacteria solution was centrifuged at 5000 rpm for 5 minutes at 4° C., collected and resuspended in ⅓ volume of AAM liquid medium, which can be used to transform a variety of acceptor materials of rice.

In this example, the immature embryo callus of *Wuyun japonica* was transformed by the conventional *Agrobacterium tumefaciens* transformation method. At 12-15 days after pollination, immature seeds of Zhonghua 11 were soaked in 70% ethanol for 1 minute and then sterilized in NaClO solution (mixed with water at the ratio of 1:3, with 2-3 drops of Tween 20 being added) for more than 90 minutes, and washed with sterile water for 4-5 times. And then the immature embryo was picked out with scalpel and tweezer, and inoculated on N6D2 medium to induce callus, incubated at 26±1° C. in darkness, which can be used for transformation after 4 days. The immature embryos callus was immersed into a fresh AAM *Agrobacterium* bacteria solution and shaked from time to time. The rice material was removed after 20 minutes (extra bacteria solution was absorbed on the sterile filter paper), transferred to N6D2C medium immediately, and co-cultured at 26° C. for 3 days. During co-culture, acetosyringone was added to the co-culture medium as an *Agrobacterium* Vir gene activator at a concentration of 100 µmol/L. After 3 days, the callus was removed from the co-culture medium, the germs were cut off and the callus was transferred to the selection medium N6D2S1 (Hyg 25 mg/l) for selective culture. After 7-12 days, the resistant calli was transferred to selection medium N6D2S2 (Hyg 50 mg/l) for further screening. After 10-12 days, the vigorous resistant calli was transferred to pre-differentiation medium for about a week, and then transferred to differentiation medium for differentiation (12 hours of light/day). The regenerated seedlings were rooted on the ½MS0H medium and then moved into artificial climate chamber for basin soil cultivation. The total DNA of the leaves was extracted after the obtained regenerated-plants were transplanted and survived, and the transformed plants were further identified by PCR. Transgenic T2 was used to observe the high temperature resistant phenotype of rice.

3.4. Detection of Expression Level in Transgenic Plant:

To verify the transgenic results, Real-time PCR was used to accurately quantify the HTR1 expression level in each transgenic line. Taking the leaves of seedling stage, RNA was extracted and reverse-transcribed into cDNA, and the expression level of HTR1 at mRNA level was detected by using TaKaRa SYBRGREEN kit. The detection primers are as follows:

5' primer sequence is:

(SEQ ID NO.: 21)
5'- CAATCTGGTGGTGTAAGACC-3';

3' primer sequence is:

(SEQ ID NO.: 22)
5'- TCCAGGAGAAGTATGACC-3'.

In the experiment, Actin was used as internal reference primer, and the primer sequence is shown as below:

5' primer sequence is:

5'- TCCATCTTGGCATCTCTCAG-3'; (SEQ ID NO.: 23)

3' primer sequence is:

5'- GTACCCTCATCAGGCATCTG -3'. (SEQ ID NO.: 24)

The results were analyzed using relative quantitative analysis. The expression level of HTR1 in the empty vector of each transgenic series was set to 1, and the expression levels of other lines were shown as a multiple of the expression level relative to the empty vector.

Wherein the total protein in plant was extracted from the HTR1-overexpressing plant, and after the total protein was separated by SDS-PAGE, anti-FLAG antibody was used to detect the accumulation of exogenous gene at protein level by western blot.

The results are shown in FIG. 4A, and both of overexpression of $HTR1^{CG14}$ and $HTR1^{WYJ}$ overexpression can enhance the high temperature resistance of rice, but the high temperature resistance of the former is stronger; Knockdown of $HTR1^{CG14}$ in NTR (CG14) will make rice more sensitive to high temperature. The above two lines were the growth status of the corresponding rice lines before and after the high temperature treatment. The below line was the expression level of HTR1 in the corresponding lines (real-time RCR data were shown for Knockdown lines, while the overexpression lines were detected for the expression level of exogenous protein by west-blotting).

Example 4

Experiments for Overexpression of $HTR1^{CG14}$ in *Arabidopsis* and Tall Fescue:

The transformation of *Arabidopsis thaliana* was carried out by *Agrobacterium tumefaciens* GV3101-mediated immersion method. $HTR1^{CG14}$-pHB was introduced into *Agrobacterium* strain GV3101 by freeze-thawing method and the strain was innoculated on a selective plate (Rif 100 μg/mL+Gm 50 μg/mL+Kan 50 μg/mL) and cultured at 28° C. for 2 to 3 days. The positive clones were picked and monoclons were selected by streaking-inoculation, and then the plasmids were extracted and transformed back to DH5α. The strain were cultured by shaking and the plasmids were extracted and verified by enzyme digestion. The correct positive *Agrobacterium* clones were used for transformation. *Agrobacterium* containing the transgenic vector was incubated overnight at 30° C. until OD600≈2.0, and centrifuged at 4,500 rpm for 10 mins. The cell pellet was suspended in freshly prepared transformation solution to a final concentration of OD600≈0.8.

The plant grown for about a month and grown well was used for transformation (before the transformation, top pinch was performed for the plant a week in advance, so that the plant can produce more buds, thereby improving the transformation efficiency). When transformed, the over-ground part of the *Arabidopsis thaliana* was soaked into the bacteria solution for 5-15 s, to ensure that all of the buds have been immersed. The excess liquid was removed with the absorbent paper, the plant was put in a sealed box to keep the humidity and stayed overnight in darkness. The next day, the plant was taken out, and vertically transferred to normal conditions for growth. The seeds of T0 generation were plated on a screening medium containing 100 g/mL Kan or 50 g/mL Hyg. Vernalization was performed at 4° C. for 48 h, and the seeds were moved to an artificial climate chamber under a condition of 24 hours of continuous light for one week. The resistant seedlings were moved to the soil to continue growing. A single insertion independent line with resistance ratio of 3:1 was selected from plants of T2 generation. After the plants of T4 generation were detected for over-expression level, the high-temperature resistance phenotype was analysed.

The genetic transformation of *Festuca arundinacea* is also mediated by *Agrobacterium tumefaciens* EHA105 as that of rice, in which leaves were infected for the induction of the callus. The positive plants were also used in the high-temperature resistance phenotyping after the overexpression level was detected.

High temperature stress was identified for the transgenic positive lines of *Arabidopsis thaliana* and tall fescue with $HTR1^{CG14}$ overexpression.

The results show that the transgenic positive plants demonstrate a significantly enhanced high temperature resistance compared with the control (FIG. 5). Therefore, besides rice, $HTR1^{CG14}$ has a wide application prospect in the high temperature resistant molecular breeding of other crops (such as cruciferous vegetables, and other vegetables, fruits and flowers effected by the high-temperature, and pastures, lawns, etc.).

Example 5

Analysis for Ubiquitination Proteome:

The over-ground part of seedlings of NIL (WYJ) and NIL (CG14) before treatment and 30 hours after high temperature (45° C.) treatment were used, the plant total protein was extracted and then enzyme digested, the anti-kGG antibody was used to enrich enzymolyzed peptide fragments of the ubiquitinated modified protein, and these peptide fragments were then subjected to mass spectrum identification by label-free method.

The experiment was divided into four groups, and the experiment was repeated for 3 times for each group, obtaining a total of 12 copies of data.

Four groups of samples were analyzed by two-way analysis of variance for screening differential genes, spots of protein for ubiquitination modification, p-value of which reached a significant level ($p<0.05$) through two-factor (genotype and high temperature treatment) variance analysis, were selected for the study.

1) Sampling. NIL(CG14) and NIL(WYJ) were used. After 12 days of water planting in the laboratory, the over-ground part of 20 seedlings of NIL (CG14) and NIL (WYJ) before treatment and 30 hours after high temperature (45° C.) treatment were respectively taken, and immediately liquid-nitrogen frozen and stored.

2) Protein cleavage and quantification. About 1 g of each sample (4 samples in total) was taken and ground into powder with liquid nitrogen and transferred to 50 ml of centrifuge tube, and 25 ml of TCA/acetone (1:9) was added, precipitated at −20° C. overnight, and centrifuged at 10,000 rpm for 45 minutes to remove the supernatant. The obtained pellet was washed by 25 ml of acetone, and centrifuged at 10,000 rpm for 45 minutes to remove the supernatant, which was repeated for 3 times. The precipitate was air dried. SDT buffer (4% SDS, 150 mM Tris-HCl pH 8.0) was added at a ratio of 10:1, mixed well by Votex, placed into a boiling water bath for 5 mins, ultrasonicated (80 w, ultrasound 10 s, intermittent 15 s, a total of 10 times), placed into a boiling water bath for 5 mins, and centrifuged to obtain the supernatant. Quantification was performed by BCA method.

3) SDS-PAGE experiment of protein. 20 μs of each sample (4 samples in total) was taken for SDS-PAGE experiment.

4) FASP enzymatic hydrolysis for protein and detection and desalination of peptide fragments. 6 mg of protein was taken from each sample (4 samples in total), DTT was added to the final concentration of 100 mM, placed into a boiling water bath for 5 mins, and cooled to room temperature. Samples were divided into 15 tubes at 400 μg/tube for the parallel enzymatic hydrolysis (sample D was divided into 20 tubes at 300 μg/tube, respectively). 200 μL of UA buffer was added to all of the sample tubes, and centrifuged at 14000 g for 15 mins, and the filtrate was discarded. 100 μL of IAA buffer (50 mM IAA in UA) was added, shaken at 600 rpm for 1 min, placed in darkness and at the room temperature for 30 mins, and centrifuged at 14000 g for 10 mins. 100 μL of UA buffer was added, and centrifuged at 14000 g for 10 mins, which was repeated twice. 100 μL of 25 mM ammonium bicarbonate solution was added and centrifuged at 14,000 g for 10 mins, repeated twice. 40 μL of Trypsin buffer (2 μg Trypsin in 25 mM ammonium bicarbonate solution) was added, and shaked at 600 rpm for 1 min, and at 37° C. for 16-18 h. A new collection tube was taken and centrifuged at 14,000 g for 10 mins, the filtrate was combined respectively according to the sample, and peptide fragments were quantificated by OD280. 2.5 μL peptide fragment was taken from each sample for mass spectrometry and library analysis using LTQ VELOS mass spectrometer (Thermo Finnigan, San Jose, Calif.). The tested peptide fragments were subjected to desalting using Sep-Pak C18 Classic Cartridge. 100 μL of solution of desalted peptide fragments was separately lyophilized and re-dissolved for mass spectrometry and library analysis, and other peptide fragments were lyophilized for further use.

5) Enrichment of ubiquitinated peptide. The digested peptide fragments were enriched by CST's PTMScan Ubiquitin Remnant Motif (K-ε-GG) Kit. The main steps were: the peptide fragments were dissolved with 1×IAP buffer, and centrifuged to remove impurities, and the supernatant was transferred to beads washed with PBS, and incubated at 4° C. for 2 hours; and then washed twice with 1×IAP buffer, washed for three times with ddH$_2$O, and finally eluted twice with 0.15% of TFA. The solutions of two eluted product were filtered through a 0.22 μm filter and lyophilized for further use.

6) LCMS/MS analysis of the enzymatic hydrolyzate. 24 μL 0.1% FA solution was added to each sample for re-dissolution. The solution of re-dissolved peptide fragments was analyzed by LCMSMS, and each sample was repeated injected for three times, with 6 μL of each injection. The separation was carried out by means of HPLC liquid-phase system EASY-nLC1000 with flow rate of nanoliter. Liquid phase A solution is 0.1% of formic acid acetonitrile aqueous solution (2% of acetonitrile), and B solution is 0.1% of formic acid acetonitrile aqueous solution (84% of acetonitrile). Columns of Thermo EASY column SC200 150 μm*100 mm (RP-C$_{18}$) were equilibrated with 100% A solution. Samples were loaded from an autosampler to Thermo EASY column SC001 traps 150 μm*20 mm (RP-Cis) (Thermo) and separated by column chromatography at a flow rate of 400 nl/min. The relevant liquid phase gradient was listed as follows: 0 minutes - - - 100 minutes, B liquid linear gradient was from 0% to 45%; 100 minutes - - - 108 minutes, B liquid linear gradient was from 45% to 100%; 108 minutes - - - 120 minutes, B liquid was maintained at 100%. The digested products were separated by capillary high performance liquid chromatography for mass spectrometry analysis using a Q-Exactive mass spectrometer (Thermo Finnigan). Analysis time: 120 min, Detection method: positive ion, scanning range of the parent ion: 300-1800 m/z, the mass and charge ratio of the polypeptide and the fragments thereof were collected according to the following method: 20 fragment maps were collected after full scan (MS$^2$ scan, HCD). resolution of MS$^1$ at M/Z 200 was 70,000 and resolution of MS$^2$ at M/Z 200 was 17,500.

7) Analysis of label-free data using Maxquant. 12 LCMS/MS raw files were imported into Maxquant software (1.3.0.5 of version number) for library analysis, for LFQ and iBAQ of label-freequantitative analysis. Maxquant's library file was analyzed using Perseus software.

The experimental results showed that high temperature treatment resulted in denaturation and ubiquitination of a large number of protein in rice cells. The amount of accumulated ubiquitinated protein was significantly decreased in NIL (CG14) than the control of NIL (WYJ) (FIG. 3B) under high temperature stress, indicating that HTR1$^{CG14}$ was more efficient in removing denatured protein, and reducing the damage of many denatured proteins induced by high temperature to the cell, thereby enhancing the heat resistance of rice.

Example 6

Preparation of Rice High Temperature Resistance Protein 1

In this example, HTR1-CG14-PTA2 in Example 3 was used as a template, primers (SEQ ID NO.:25 and 26) were designed based on the nearby region of start codon and the stop codon of SEQ ID NO: 1, and amplification was performed with high fidelity Taq enzyme of pfuTaq (available from STRATAGENE, La Jolla, Calif.), thereby obtaining amplified products of HTR1-CG14-BS.

Wherein 5' oligonucleotide primer sequence is:

(SEQ ID NO.: 25)
5'- CGGGATCCATGGGCGACAGCCAGTACTCCTTCTCCC-3';

3' primer sequence is:

(SEQ ID NO.: 26)
5'- GCGTCGACTTATTCCACCTCTTCCAAGAAATCCTTG-3'.

The amplified product was recombinantly added into a pTA2 vector (available from TOYOBO, Japan.) with a normal Taq enzyme plus A. The recombinant was digested, identified and sequenced. PTA2 recombinantly containing HTR1-CG14-BS was digested with BamH I and Sal I, and the target fragments were recovered and purified;

pET32a (+)(available from Novagen, Madison, Wis., USA.) digested with BamH I and Sal I was ligated with T4 ligase. The recombinant was identified by digestion with BamH I and Sal I. The correct recombinant was sequenced, the reading frame and the sequence were verified. The prokaryotic expression vector pET32a (+), which recombinantly contained HTR1, was transferred into *Escherichia coli* DH5α, prokaryotic expression was induced by IPTG, and then the protein was purified by His-tag column.

The purified and labeled HTR1 protein was obtained; after the label was removed by digestion, 12% of SDS-PAGE gel was used for electrophoresis; and the molecular weight of the protein was identified as about 26 Kda.

Results and Discussion

1. The chromosome segment substitution line (CSSL) constructed by using African cultivated rice variety CG14 as a donor and *japonica* rice cultivar of Wu Yun *japonica* as a receptor parent was screened at high temperature. After verified for many times, a substitution line demonstrating a significant high temperature resistant property was obtained, wherein the substitution line contained HTR1 site (HTR1$^{CG14}$) from the CG14. Based on this line, the near-isogenic line of NIL (CG14) containing HTR1$^{CG14}$ was successfully cultivated and meantime the control line of NIL(WYJ) was also obtained by means of backcrossing with recurrent parent of Wu Yun *japonica* (WYJ) and molecular marker-assisted selection (MAS). The growth and development of NIL (CG14) under normal growth conditions were not different from those of control NIL (WYJ), and the final yield was also consistent with that of the control (FIG. 2A, B), however, it was more resistant to high temperature than the control at seedling stage or adult-plant stage (FIG. 2A). Especially, the yield of NIL (CG14) was significantly higher than that of the control (FIG. 2C, D), when high temperature treatment was performed during the flowering period and the filling period which are sensitive to high temperature. These data indicate that this high temperature resistant gene locus has a good application value in the high temperature resistant molecular breeding of rice.

2. HTR1 gene was cloned by map-based cloning method. Bioinformatics analysis shows that HTR1 encodes α2 subunit of 26S proteasome. The genomic sequence and cDNA sequence of HTR1 were cloned by high fidelity PCR (FIG. 1). Sequence analysis shows that the genome length of HTR1 is about 6292 bp (SEQ ID NO.: 29) and 6,289 bp (SEQ ID NO.: 30), with a promoter region of about 2 kb (SEQ ID NO.: 27, 28). Comparing the promoters between the two parents, it is found that there are nine single nucleotide differences (SNPs) and one deletion containing 3 bases in the 2 kb of sequence in CG14, compared with WYJ. This difference in the promoter allows the HTR1$^{CG14}$ from CG14 to more efficiently respond to high temperatures at the expression level, i.e., the promoter more efficiently responds to high temperatures (FIGS. 3A and 3C). Wherein, the experiment demonstrating that the promoter drives expression of self genes induced by high temperature is shown in FIG. 3A, while the experiment demonstrating that the promoter drives expression of GUS gene induced by high temperature is shown in FIG. 3C.

3. Through Comparing cDNA and genomic sequence, it was found that HTR1 gene contains 11 exons and 10 introns. The length of full length ORF (open reading-frame) is 708 bp, encoding 235 amino acids (FIG. 1). Compared with the sequences derived from different parents, it is found that there are 3 base mutations in ORF region of HTR1$^{CG14}$ in high temperature resistant African cultivated rice CG14, compared with the allele HTR1$^{WYJ}$ from *Wuyun jing*, wherein two of the mutations are synonymous mutations (C to T at positions 222 and 543), and the base mutation at position 296 (A to G) results in amino acid substitution (from WYJ$^{Arg}$ to CG14$^{His}$), which affected the function and activity of HTR1 protein, thereby allowing the rice have a different high temperature resistance (FIG. 1, 2, 4A). Wherein the SNP at position 222 (C to T) have not resulted in a change in the encoded sequence of the protein, but we have found that the SNP represents a haplotype of HTR1. That is, the SNP can be used to identify haplotypes of HTR1 in different rice cultivars.

4. Through studying the expression pattern of HTR1, it was shown that HTR1 is universally expressed in various tissues of rice, and its expression is significantly induced by high temperature (FIG. 3A, C), indicating that the gene plays an important role in the high temperature response of rice. Through comparison of expression patterns of HTR1 from different sources, it was found that the expression of HTR1$^{CG14}$ from CG14 is about 1 times higher than that of HTR1$^{WYJ}$ in various tissues. Furthermore, HTR1$^{CG14}$ is more significantly induced by high temperature, the expression level of which is significantly higher than that in HTR1$^{WYJ}$ during the high temperature treatment (FIG. 3A), indicating that HTR1$^{CG14}$ can more efficiently respond to high temperature at the expression level, that is, the promoter thereof can more efficiently respond to high temperature.

5. Systematic studies on ubiquitinated proteins accumulated in the cell of NIL (CG14) and their controls under high temperature treatment have shown that large amounts of protein were denaturated in cells and further ubiquitinated due to high temperature. However, under the high temperature stress, the amount of accumulated and ubiquitinated protein was significantly decreased in NIL (CG14) than the control of NIL (WYJ) (FIG. 3B), indicating that HTR1' was more efficient in removing denatured protein, reducing the damage of many denatured proteins induced by high temperature to the cell, and better maintaining the dynamic balance of protein under stress, thereby enhancing the heat resistance of rice. This is a new mechanism for the response of plants to high temperatures. It was assumed that renaturation of denatured proteins mediated by high temperature-induced heat shock protein were the most important way for plants to respond to high temperatures. While we have found that in the case of more intense high temperature stress, the plants die due to a large number of toxic denatured proteins produced in the cells. At this time, these toxic proteins can be rapidly and effectively removed by the protein ubiquitin degradation pathway, recovered and recycled, thereby protecting the cell activity, which is a more important new mechanism on heat resistance.

6. The high expression of HTR1$^{CG14}$ and HTR1$^{WYJ}$ in the recurrent parent of *Wuyun jing* can enhance the high temperature resistance thereof, wherein the high temperature resistance of HTR1$^{CG14}$ overexpressing plants is stronger (FIG. 4A). The knockdown of HTR1 in NIL (CG14) can significantly reduce the high temperature resistance of rice (FIG. 4A). These transgenic experiments confirm that this gene is indeed a functional gene that regulates the high temperature tolerance of rice. The growth and yield of HTR1$^{CG14}$ overexpressing transgenic rice under normal growth conditions were not different from that of the transgenic negative control (FIG. 4A, B). However, under the high temperature stress, in the transgenic rice with overexpression of HTR1$^{CG14}$ can not only exhibit significantly increased viability of the seedling stage (FIG. 4A); the yield is significantly higher than that of the control especially when suffered from high temperature during the flowering stage and grain filling stage. This indicates that HTR1$^{CG14}$ gene is a good genetic resource for improving the high temperature resistance of crops and can be used to enhance the high temperature resistance of crops through genetic engineering and to ensure food security under global climate deterioration.

7. Overexpression of HTR1$^{CG14}$ in *Arabidopsis thaliana* and *Festuca arundinacea* Scherb can significantly enhance the high temperature resistance of transgenic positive plants (FIG. 5). Both basic high temperature resistance and adaptive high temperature resistance can be significantly enhanced in *Arabidopsis* overexpressing HTR1$^{CG14}$ (FIG. 5

A-F). These results indicate that, besides rice, HTR1$^{CG14}$ also has a good application prospect in the high temperature resistant breeding of other crops (such as cruciferous vegetables, and other vegetables, fruits and flowers affected by the high-temperature, and pastures, lawns, etc.).

8. Studies on mutants of some other 26S proteasome subunits of Arabidopsis thaliana have shown that plants will exhibit a high temperature-sensitive phenotype after mutations in 26S proteasome subunit (FIG. 6, A-F). This further demonstrates the important role of the 26S proteasome-mediated ubiquitination pathway in the high temperature response process of plants. It was found that of if rice was treated with the 26S proteasome degradation activity inhibitor MG132 during the high temperature treatment, the plants will exhibit high temperature sensitive phenotype by blocking the 26S proteasome degradation pathway during high temperature response (FIG. 6G, H). That is, the high temperature resistance of the plant is significantly reduced by inhibiting the 26S proteasome degradation activity using 26S proteasome degradation activity inhibitor.

9. HTR1 is very conservative in eukaryotes (FIG. 7). There is also a highly homologous gene PAB2 in rice, whereas in other monocotyledonous plants (including maize, sorghum, Brachypodium distachyon, and ancestral species of wheat, etc.), the similarity of homologous protein is 99%-100%; in all of higher plants, the similarity of homologous proteins is substantially also more than 95% (94% only in Arabidopsis); homologous proteins of the protein are present in algae and fungi, and the sequence is conserved; even in animals, its homologous protein is also existed; and the similarity of homologous protein in the vertebrate and HTR1 protein can also reach more than 80% (FIG. 7). The experimental results that such high conservativeness and overexpression of the protein in Arabidopsis thaliana and tall fescue can enhance its high temperature resistance show that HTR1 also has a function of increasing high temperature resistance in other crops.

10. The distribution of HTR1 in different haplotypes of rice was significantly correlated with the growth temperature of the corresponding cultivars (FIG. 8A, B). HTR1$^{CG14}$ represents a haploid type that is specifically present in African rice, and this haplotype can significantly enhance the high temperature resistance of rice (FIG. 8A). There are also different haplotypes of HTR1 in Asian rice, wherein three SNPs can represent the genotype of haplotype thereof (FIG. 8B). The high temperature resistance of rice varieties with different haploid was significantly correlated with the expression of HTR1 (FIG. 8C-E). This indicates that not only overexpression of HTR1 can enhance the high temperature resistance of rice, but also the haploid difference of HTR1 in different cultivars can lead to the difference in high temperature resistance, which provides a good basis for the introduction of rice.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for obtaining a high temperature resistant line of a plant, wherein the method comprises steps of:
(a) transforming plant cells with a recombinant DNA construct, wherein said recombinant DNA construct comprises a polynucleotide molecule which comprises a promoter operably linked to a nucleotide sequence encoding a rice α2 subunit protein of 26S proteasome having an amino acid sequence, wherein the amino acid at position 99 is mutated from histidine to arginine as compared to the corresponding amino acid position 99 in the amino acid sequence of SEQ ID NO: 4, wherein said rice α2 subunit protein of 26S proteasome is selected from the group consisting of (i) the α2 subunit protein of 26S proteasome of rice having the amino acid sequence as set forth in SEQ ID NO: 2, and (ii) an α2 subunit protein of 26S proteasome of rice having an amino acid sequence which has at least 95% amino acid sequence identity to the amino acid sequence of SEQ ID NO: 2, wherein said transformation is through *Agrobacterium tumefaciens* mediated transformation, and wherein said transformation results in stable integration of said recombinant DNA construct into the genome of said transformed plant cells;
(b) regenerating transformed plants from said transformed plant cells; and
(c) selecting a transformed plant from step (b), which overexpresses said rice α2 subunit protein of 26S proteasome, and exhibits high temperature resistance when grown under a high temperature stress as compared to a control plant of the same species grown under identical conditions.

2. The method of claim 1, wherein said rice α2 subunit protein of 26S proteasome has one or more characteristics selected from the group consisting of:
(i) after degradation and denaturation treatment under said high temperature stress, the activity of said rice α2 subunit protein of 26S proteasome is significantly higher than the activity of the polypeptide as shown in SEQ ID NO: 4 subjected to identical degradation and denaturation treatment; and
(ii) under said high temperature stress, the stability of said rice α2 subunit protein of 26S proteasome is significantly higher than the stability of the polypeptide as shown in SEQ ID NO: 4 subjected to said high temperature stress condition.

3. The method of claim 1, wherein said rice α2 subunit protein of 26S proteasome is set forth in SEQ ID NO: 2.

4. The method of claim 1, wherein said plant cells are selected from the group consisting of rice, maize, sorghum and wheat.

5. The method of claim 1, wherein the nucleotide sequence encoding said rice α2 subunit protein of 26S proteasome is selected from the group consisting of:
the nucleotide sequence as set forth in SEQ ID NO: 1, and
the nucleotide sequence as set forth in SEQ ID NO: 29.

6. The method of claim 1, wherein said promoter is a high temperature stress responsive promoter, and wherein said high temperature stress is from 35° C. to 45° C.

7. The method of claim 1, wherein said promoter is set forth in SEQ ID NO: 27.

8. The method of claim 1, wherein the nucleotide sequence encoding said rice α2 subunit protein of 26S proteasome is set forth in SEQ ID NO: 1.

* * * * *